United States Patent
Sung et al.

(10) Patent No.: US 7,282,220 B1
(45) Date of Patent: *Oct. 16, 2007

(54) GENIPIN-CROSSLINKED GELATIN MICROSPHERES AS DRUG CARRIER

(76) Inventors: Hsing-Wen Sung, 7F, No. 15, Alley 7, Lane 298, Section 2, Kung-Fu Road, Hsinchu (TW) 300; Huang-Chien Liang, No. 19, Lane 101, Chu-Lien Street, Hsinchu (TW) 300; Wen-Hsiang Chang, 1F., No. 38, Sec. 1, Jnan Rd., Wenshan Chiu, Taipei (TW) 116; Hosheng Tu, 15 Riez, Newport Beach, CA (US) 92657

(*) Notice: Subject to any disclaimer, the term of this patent is extended or adjusted under 35 U.S.C. 154(b) by 842 days.

This patent is subject to a terminal disclaimer.

(21) Appl. No.: 10/622,303

(22) Filed: Jul. 18, 2003

Related U.S. Application Data

(63) Continuation-in-part of application No. 09/297,808, filed as application No. PCT/US97/20113 on Nov. 4, 1997, now Pat. No. 6,608,040.

(60) Provisional application No. 60/398,003, filed on Jul. 23, 2002, provisional application No. 60/030,701, filed on Nov. 5, 1996.

(51) Int. Cl.
*A61K 9/14* (2006.01)
*A61K 9/50* (2006.01)

(52) U.S. Cl. .................. 424/489; 424/501; 424/423

(58) Field of Classification Search .............. 514/1, 514/4, 11, 26, 356; 424/422, 423, 445
See application file for complete search history.

(56) References Cited

U.S. PATENT DOCUMENTS

| | | | |
|---|---|---|---|
| 3,929,992 A | 12/1975 | Sehgal et al. | |
| 4,806,595 A | 2/1989 | Noishiki et al. | |
| 5,037,664 A | 8/1991 | Kyogoku et al. | |
| 5,270,446 A | 12/1993 | Kyogoku et al. | |
| 5,322,935 A | 6/1994 | Smith | |
| 5,516,781 A | 5/1996 | Morris et al. | |
| 5,521,154 A | 5/1996 | Garlick et al. | |
| 5,763,579 A * | 6/1998 | Gagnieu et al. | ............ 530/356 |
| 5,780,052 A | 7/1998 | Khaw et al. | |
| 5,783,214 A * | 7/1998 | Royer | .................. 424/499 |
| 5,886,016 A | 3/1999 | Talley et al. | |
| 5,929,038 A | 7/1999 | Chang | |
| 6,103,255 A | 8/2000 | Levene et al. | |
| 6,162,826 A | 12/2000 | Moon et al. | |
| 6,206,931 B1 | 3/2001 | Cook et al. | |
| 6,262,083 B1 | 7/2001 | Moon et al. | |
| 6,264,992 B1 | 7/2001 | Voytik-Harbin et al. | |
| 6,287,285 B1 * | 9/2001 | Michal et al. | ............ 604/264 |
| 6,395,300 B1 | 5/2002 | Straub et al. | |
| 6,545,042 B2 | 4/2003 | Sung et al. | |
| 6,545,097 B2 * | 4/2003 | Pinchuk et al. | ............ 525/240 |
| 6,624,138 B1 * | 9/2003 | Sung et al. | .................. 514/1 |
| 6,998,418 B1 * | 2/2006 | Sung et al. | ................ 514/456 |
| 7,101,857 B2 * | 9/2006 | Sung et al. | .................. 514/26 |
| 2003/0004533 A1 * | 1/2003 | Dieck et al. | ................ 606/191 |

FOREIGN PATENT DOCUMENTS

WO    WO 9819718 A1 *  5/1998

OTHER PUBLICATIONS

Mi FL, Sung HW, and Shyu SS, Carbohydrate Polymers 2002; 48: 61-72.
Mi FL, Tan YC, Liang HF and Sung HW, Biomaterials 2002; 23: 181-191.
Chang Y, Tsai CC, Liang HC and Sung HW, J Thorac Cardiovasc Surg 2001; 122: 1208-1218.
Mi FL, Sung HW and Shyu SS, J Polym Sci A: Polym Chem 2000; 38: 2804-2814.
Sung HW, Chang Y, Liang IL, Chang WH and Chen YC, J Biomed Mater Res 2000; 52: 77-87.
Huang LLH, Sung HW, Tsai CC and Huang DM, J. Biomed Mater Res 1998; 42: 568-576.
Sung HW, Huang RN, Huang LLH, Tsai CC and Chiu CT, J Biomed Mater Res 1998; 42: 560-567.
Sung HW, Huang DM, Chang WH, Huang RN and Hsu JC, J Biomed Mater Res 1999; 46: 520-530.
Sung HW, Huang DM, Chang WH, Huang LLH, Tsai CC and Liang IL; J Biomater Sci Polymer Edn. 1999; 10(7): 751-771.
Liang HC, Chang WH, Lin KJ and Sung HW, J Biomed Mater Res 2003; 65A: 271-282.

* cited by examiner

*Primary Examiner*—Brian Kwon

(57) ABSTRACT

A pharmaceutical microsphere comprises a bioactive agent and a biological carrier that encapsulates the bioactive agent, wherein the biological carrier is crosslinked with a crosslinking agent.

6 Claims, 12 Drawing Sheets

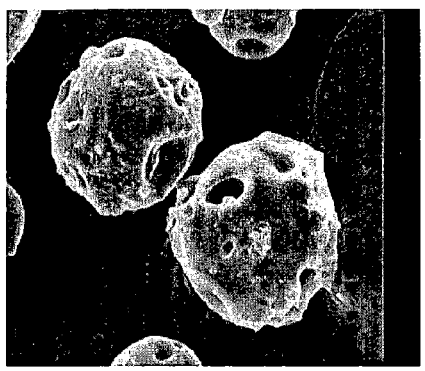
FIG. 4A
GP
Degradation with Collagenase
GA
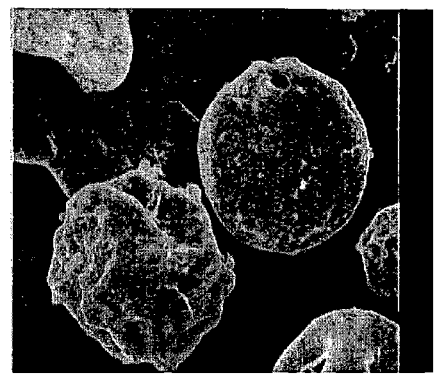
FIG. 4B
GP
Degradation without Collagenase
GA
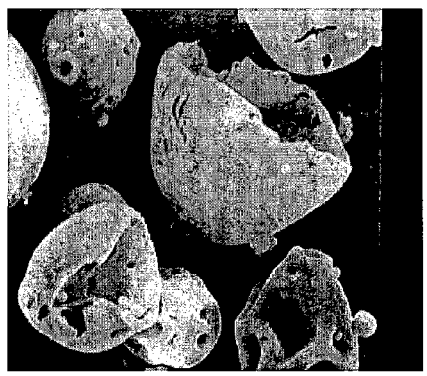
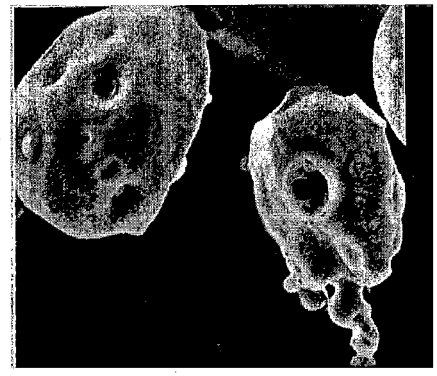
----- stands for 50 μm Fickian diffusion Case-II transport anomalous diffusion

GENIPIN-CROSSLINKED GELATIN MICROSPHERES AS DRUG CARRIER

CROSS-REFERENCE TO RELATED APPLICATIONS

This patent application is a continuation-in-part application of application Ser. No. 09/297,808 filed Sep. 27, 2001 now U.S. Pat. No. 6,608,040, entitled "Chemical modification of biomedical materials with genipin", which is the national stage entry of PCT/US97/20113 filed Nov. 4, 1997, which claims the benefits of a provisional application Ser. No. 60/030,701 filed Nov. 5, 1996. This patent application also claims the benefits of a provisional application Ser. No. 60/398,003 filed Jul. 23, 2002, entitled "Genipin-crosslinked gelatin microspheres as a drug carrier", incorporated herein by reference in its entirety.

FIELD OF THE INVENTION

The present invention generally relates to chemical modification of biomedical materials, such as collagen, elastin or gelatin matrix with a naturally occurring crosslinking reagent, genipin. More particularly, the present invention relates to gelatin microspheres as drug carriers, wherein the microspheres are chemically treated with a crosslinking reagent, genipin, its derivatives or analog and the process thereof.

BACKGROUND OF THE INVENTION

Crosslinking of Biological Material

Crosslinking of biological molecules is often desired for optimum effectiveness in biomedical applications. For example, collagen, which constitutes the structural framework of biological tissue, has been extensively used for manufacturing bioprostheses and other implanted structures, such as vascular grafts, wherein it provides a good medium for cell infiltration and proliferation. More recently, collagenous material, such as collagen, elastin or gelatin is used as drug carriers. However, biomaterials derived from collagenous tissue or collagenous material must be chemically modified and subsequently sterilized before they can be used in humans. The fixation, or crosslinking, of collagenous material increases biodurability and reduces antigenicity and immunogenicity. In one aspect of the present invention, crosslinking of a drug-containing biological material with genipin enables the resulting material ("biological substance") with less antigenicity or immunogenicity, wherein the biological material comprises collagen, gelatin, elastin, chitosan, NOCC, and the like that has at least one amino functional group for reaction with genipin.

Clinically, biological tissue material has been used in manufacturing heart valve prostheses, small-diameter vascular grafts, biological patches, venous valve bioprostheses, bioadhesives, ligament replacement, stent coverings, and wound dressings, among others. However, the biological tissue material has to be fixed with a crosslinking or chemically modifying agent and subsequently sterilized before they can be used in humans. The fixation of biological tissue or collagen is to reduce antigenicity and immunogenicity and prevent enzymatic degradation. Various crosslinking agents have been used in fixing biological tissue. These crosslinking agents are mostly synthetic chemicals such as formaldehyde, glutaraldehyde, dialdehyde starch, glyceraldehydes, cyanamide, diimides, dimethyl adipimidate, diisocyanates, and epoxy compound. However, these chemicals are all highly cytotoxic which may impair the biocompatibility of biological tissue. Of these, glutaraldehyde is known to have allergenic properties, causing occupational dermatitis and is cytotoxic at concentrations greater than 10-25 ppm and as low as 3 ppm in tissue culture. It is therefore desirable to provide a crosslinking agent (synonymous to a crosslinking reagent) suitable for use in biomedical applications that is within acceptable cytotoxicity and that forms stable and biocompatible crosslinked products.

An example of a genipin-crosslinked heart valve is reported by Sung et al., a co-inventor of the present invention, (Journal of Thoracic and Cardiovascular Surgery vol. 122, pp. 1208-1218, 2001) entitled *Reconstruction of the right ventricular outflow tract with a bovine jugular vein graft fixed with a naturally occurring crosslinking agent (genipin) in a canine model*, entire contents of which are incorporated herein by reference. Sung et al. herein discloses genipin and its crosslinking ability to a collagen-containing biological tissue heart valve.

To achieve this goal, a naturally occurring crosslinking agent (genipin) has been used to fix biological tissue. The co-pending application Ser. No. 09/297,808 filed Sep. 27, 2001, entitled "Chemical modification of biomedical materials with genipin" is incorporated and cited herein by reference. The cytotoxicity of genipin was previously studied in vitro using 3T3 fibroblasts, indicating that genipin is substantially less cytotoxic than glutaraldehyde (Sung H W et al., J Biomater Sci Polymer Edn 1999; 10:63-78). Additionally, the genotoxicity of genipin was tested in vitro using Chinese hamster ovary (CHO-K1) cells, suggesting that genipin does not cause clastogenic response in CHO-K1 cells (Tsai C C et al., J Biomed Mater Res 2000; 52:58-65), incorporated herein by reference. A biological material (including collagen, elastin, chitosan, or gelatin-containing substrate) treated with genipin resulting in acceptable cytotoxicity is key to biomedical applications.

Sung and Liang in U.S. Pat. No. 6,545,042 entitled Acellular Biological Material Chemically Treated with Genipin, entire contents of which are incorporated herein by reference, disclose an acellular tissue providing a natural microenvironment for host cell migration to accelerate tissue regeneration. The genipin-treated biological biomaterial has reduced antigenicity and immunogenicity.

Kyogoku et al. in U.S. Pat. No. 5,037,664, U.S. Pat. No. 5,270,446, and EP 0366998 teach the crosslinking of amino group containing compounds with genipin and the crosslinking of genipin with chitosan. They also teach the crosslinking of iridoid compounds with proteins which can be vegetable, animal (collagen, gelatin) or microbial origin. However, they do not teach the use of the crosslinked products as biocompatible drug carriers.

Smith in U.S. Pat. No. 5,322,935 teaches the crosslinking of chitosan polymers and then further crosslinking again with covalent crosslinking agents like genipin and glutaraldehyde. Smith, however, does not teach the use of the cross-linked products as biocompatible drug carriers.

Drugs for Therapeutic Use

In an attempt to prevent restenosis or reduce intimal smooth muscle cell proliferation following angioplasty, numerous pharmaceutical agents have been employed clinically, concurrent with or following angioplasty. Most pharmaceutical agents employed in an attempt to prevent or reduce the extent of restenosis have been unsuccessful. The following list identifies several of the agents for which favorable clinical results have been reported: lovastatin (Sahni, R., Circulation 1989; 80 (Suppl.):65; Gellman, J., J. Am. Coll. Cardiol. 1991; 17:251); thromboxane $A_2$ synthetase inhibitors such as DP-1904 (Yabe, Y., Circulation 1989; 80 (Suppl.):260); eicosapentanoic acid (Nye, E., Aust. N.Z. J. Med. 1990; 20:549); ciprostene (a prostacyclin analog) (Demke, D., Brit. J. Haematol 1990; 76 (Suppl.):20; Darius, H., Eur. Heart J. 1991; 12 (Suppl.):26); trapidil (a platelet derived growth factor) (Okamoto, S., Circulation 1990; 82 (Suppl.):428); angiotensin convening enzyme inhibitors (Gottlieb, N., J. Am. Coll. Cardiol. 1991; 17 (Suppl. A):81A); and low molecular weight heparin (de Vries, C., Eur. Heart J. 1991; 12 (Suppl.):386), entire contents of the above-referred drugs and their therapeutic effects are incorporated herein by reference. It is one aspect of the present invention to provide site-specific administration of the pharmaceutical agents disclosed in this invention to the target site for effective therapy via a genipin-crosslinked chitosan, collagen, elastin or gelatin-containing biological microspheres carrier.

Many compounds have been evaluated in a standard animal model. The immunosuppressive agent cyclosporin A has been evaluated and has produced conflicting results. Jonasson reported that cyclosporin A caused an inhibition of the intimal proliferative lesion following arterial balloon catheterization in vivo, but did not inhibit smooth muscle cell proliferation in vitro. (Jonasson, L., Proc. Natl. Acad. Sci. 1988; 85:2303). Ferns reported that when de-endothelialized rabbits were treated with cyclosporin A, no significant reduction of intimal proliferation was observed in vivo. Additionally, intimal accumulations of foamy macrophages, together with a number of vacuolated smooth muscle cells in the region adjacent to the internal elastic lamina were observed, indicating that cyclosporin A may modify and enhance lesions that form at the sites of arterial injury. (Ferns, G. A., Circulation 1989; 80 (Supp): 184; Ferns, G., Am. J. Path. 1990; 137:403).

Morris et al. in U.S. Pat. No. 5,516,781 disclosed Rapamycin (also known as sirolimus), a macrocyclic triene antibiotic produced by Streptomyces hygroscopicus that has been shown to prevent the formation of humoral (IgE-like) antibodies in response to an albumin allergic challenge (Martel, R., Can. J. Physiol. Pharm. 1977; 55:48), inhibit murine T-cell activation (Staruch, M., FASEB 1989; 3:3411), prolong survival time of organ gratis in histoincompatible rodents (Morris, R., Med. Sci. Res. 1989; 17:877), and inhibit transplantation rejection in mammals. Rapamycin blocks calcium-dependent, calcium-independent, cytokine-independent and constitutive T and B cell division at the G1-S interface. Rapamycin inhibits gamma-interferon production induced by Il-1 and also inhibits the gamma-interferon induced expression of membrane antigen. (Morris, R. E., Transplantation Rev. 1992; 6:39). The use of rapamycin in preventing coronary graft atherosclerosis (CGA) in rats has been disclosed by Meiser (J. Heart Lung Transplant 1990; 9:55). Arterial thickening following transplantation, known as CGA, is a limiting factor in graft survival that is caused by a chronic immunological response to the transplanted blood vessels by the transplant recipient's immune system (Dec. G, Transplantation Proc. 1991; 23:2095 and Dunn, M. Lancet 1992; 339:1566).

Further, Morris et al. in U.S. Pat. No. 5,516,781 claims a new use of rapamycin for preventing CGA, in that CGA does not involve injury to the recipients' own blood vessels; it is a rejection type response. The disclosed patent '781 is related to vascular injury to native blood vessels. The resulting intimal smooth muscle cell proliferation does not involve the immune system, but is growth factor mediated. For example, arterial intimal thickening after balloon catheter injury is believed to be caused by growth factor (PGDF, bFGF, TGFb, IL-1 and others)-induced smooth muscle cell proliferation and migration. (Ip, J. H., J. Am. Coll. Cardiol 1990; 15:1667). Ferns has also shown that the immune response is not involved in arterial intimal thickening following balloon catheterization, as he found that there was no difference in intimal thickening between arteries from athymic nude rats (rats lacking T-cells) and normal rats after balloon catheterization (Am. J. Pathol. 1991; 138:1045). The above-cited patent (U.S. Pat. No. 5,516,781) and literatures are incorporated herein by reference.

In the past, polymer or plastic materials have been used as a carrier for depositing a drug or pharmaceutical agent onto the periphery of a stent to treat restenosis. One example is U.S. Pat. No. 5,886,016 to Hunter et al., entire contents of which are incorporated herein by reference. Hunter et al. discloses a method for treating a tumor excision site, comprising administering to a patient a composition comprising paclitaxel, or an analogue or derivative thereof, to the resection margin of a tumor subsequent to excision, such that the local recurrence of cancer and the formation of new blood vessels at said site is inhibited. The composition further comprises a polymer, wherein the polymer may comprise poly (caprolactone), poly(lactic acid), poly(ethylene-vinyl acetate), and poly(lactic-co-glycolic) acid.

In another example, Biocompatibles PC (phosphorylcholine by Biocompatibles) has been added as a drug carrier or surface modifier for treating tissue injury due to angioplasty and/or stenting. The technique comprises a hydrophobic component that aids in the initial adhesion and film-formation of the polymer onto the stainless steel stent substrate, and other groups allow cross-linking both within the polymer and with the stent surface to achieve firm anchorage. The coating is thus tenaciously adhered to the stent and can survive balloon expansion without damage. A therapeutic drug can be loaded within the coated substrate, such as phosphorylcholine. In another aspect of the invention, PC can be loaded into a biological material (gelatin, elastin, collagen, or chitosan) and crosslinked with genipin as a microsphere drug carrier or onto a stent.

Drugs are usually admixed or entrapped physically within the polymer framework for slow drug release. The plastic polymer which is suitable as a drug carrier may not be biocompatible, whereas some biocompatible plastic polymer may not be able to contain a specific drug and release drug in an effective timely manner for effective therapies. Therefore, there is a clinical need to have a biocompatible drug carrier that releases an effective quantity of drug over a period of time for prolonged therapeutic effects.

In a co-pending patent application by two of the present co-inventors (Sung and Tu), Ser. No. 10/211,656 filed Aug. 2, 2002 entitled "Solidifiable Biological Material Chemically Treated with Genipin", entire contents of which are incorporated herein by reference, discloses a collagen-drug-genipin compound coated onto a stent for treating proliferation and restenosis problems. In addition to collagen, the biological material or carrier may include gelatin, elastin, chitosan and the like.

In accordance with the present invention there is provided genipin treated gelatin microspheres loaded with drug for implant and other surgical applications which have shown to exhibit many of the desired characteristics important for optimal therapeutic function. In particular, the crosslinked gelatin-drug compound with drug slow release capability may be suitable as anti restenosis agent in treating atherosclerosis and other therapeutic applications.

SUMMARY OF THE INVENTION

In general, it is an object of the present invention to provide a biological substance configured and adapted for drug slow release. In one aspect of the present invention, the biological substance may be a microsphere crosslinked with a crosslinking agent enabling the microsphere to slowly release drug from the biological substance. The "biological substance" is herein intended to mean a substance made of drug-containing biological material that is fabricated to be biocompatible after a crosslinking process with a crosslinker, such as genipin. In one embodiment, the crosslinker may further comprise epoxy compounds, dialdehyde starch, glutaraldehyde, formaldehyde, dimethyl suberimidate, carbodiimides, succinimidyls, diisocyanates, acyl azide, ultraviolet irradiation, dehydrothermal treatment, tris(hydroxymethyl)phosphine, ascorbate-copper, glucose-lysine and photo-oxidizers, or the like. The "biological material" is intended herein to mean collagen, gelatin, elastin, chitosan, N, O, Carboxylmethyl Chitosan (NOCC), and the like that could be crosslinked with a crosslinker (also known as a crosslinking agent).

In one embodiment, the process of preparing a biological substance comprises steps of mixing drugs with the biological material, shaping the drug-containing biological material, followed by crosslinking with genipin. The genipin referred herein is broadly consisted of the naturally occurring compound as shown in FIG. 11 and its derivatives, analog, stereoisomers and mixtures thereof as shown in Formulas 1-4. In another embodiment, the drug-containing biological material is further coated or adhered onto a substrate before or after crosslinking with a crosslinker (such as genipin). The biological material is herein broadly generally referred to collagen, elastin, gelatin, chitosan, NOCC, the mixtures thereof, and derivates, analog and mixtures thereof. The biological material may be in a form or phase of solution, paste, gel, suspension, colloid or plasma that is fabricatable and that is solidifiable thereafter.

It is another object of the present invention to provide a method for drug slow release from a medical device comprising entrapping drug within a biological material or carrier crosslinked with genipin. The medical device can be a pill, a capsule, a gel, a microsphere or the like for the intended drug slow release.

It is a further object of the present invention to provide a method for drug slow release from an implant comprising loading drug within a biological material or carrier crosslinked with genipin, wherein the drug has an amine or amino group branch. In one aspect of the present invention, the amine or amino group of the drug is reacted with the amino group of collagen through a crosslinker, such as genipin.

Some aspects of the invention provide a pharmaceutical microsphere, comprising: a bioactive agent; and a biological carrier that encapsulates the bioactive agent, wherein the biological carrier is crosslinked with a crosslinking agent. Further, some aspects of the invention provide a method for administering a pharmaceutical microsphere into a body of a patient comprising: providing the pharmaceutical microsphere that comprises a bioactive agent and a biological carrier, the biological carrier encapsulating the bioactive agent, wherein the biological carrier is crosslinked with a crosslinking agent; and delivering or introducing the pharmaceutical microsphere into the body for therapeutic treatment.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

FIGS. 4A and 4B are SEM micrographs of the glutaraldehyde- (GA) and genipin-crosslinked (GP) gelatin microspheres at 1-day after degradation with or without collagenase.

DETAILED DESCRIPTION OF EXEMPLARY EMBODIMENTS

The following detailed description is of the best presently contemplated modes of carrying out the invention. This description is not to be taken in a limiting sense, but is made merely for the purpose of illustrating general principles of embodiments of the invention.

Figure 11:
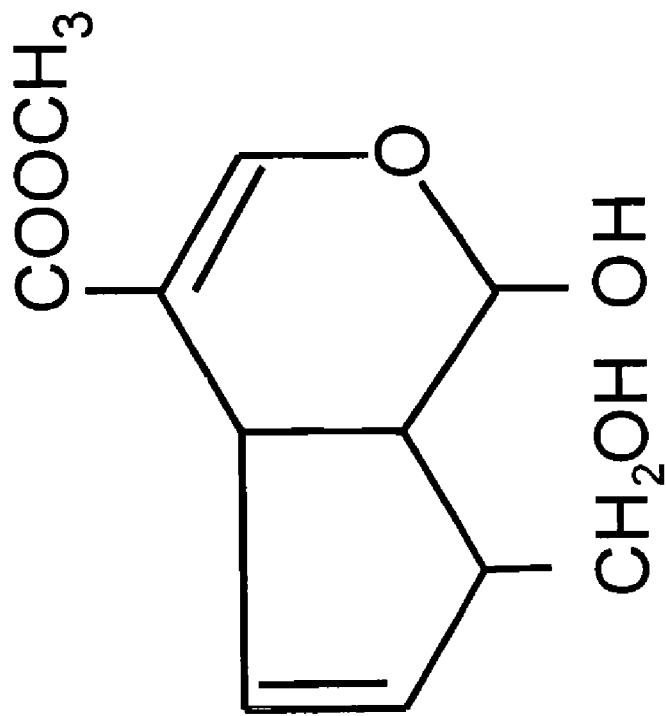
FIG. 11 are chemical structures of glutaraldehyde and genipin that are used in the chemical treatment examples of the current invention.
Figure 11:
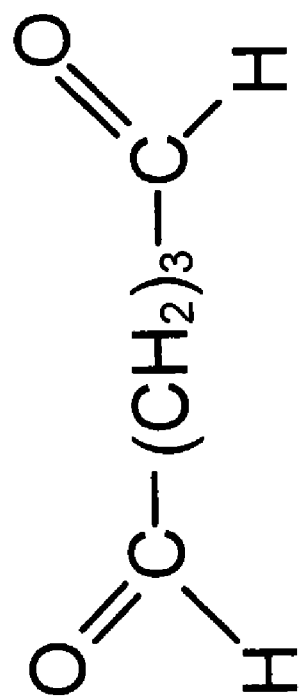

"Genipin" in this invention is meant to refer to the naturally occurring compound as shown in FIG. 11 and its derivatives, analog, stereoisomers and mixtures thereof (shown in Formulas 1-4 below).

"Crosslinking agent" is meant herein to indicate a chemical agent that could crosslink two molecules, such as genipin, epoxy compounds, dialdehyde starch, glutaraldehyde, formaldehyde, dimethyl suberimidate, carbodiimides, succinimidyls, diisocyanates, glyceraldehydes, cyanamide, diimides, dimethyl adipimidate acyl azide, ultraviolet irradiation, dehydrothermal treatment, tris(hydroxymethyl) phosphine, ascorbate-copper, glucose-lysine and photo-oxidizers, and the like.

"Biological material" or "biological carrier" is herein meant to refer to collagen extract, soluble collagen, elastin, gelatin, chitosan, NOCC, and derivates, analog and mixtures thereof and/or other collagen-containing biological material. For a preferred aspect of the present invention, the biological material is meant to indicate a fabricatable and solidifiable biological substrate comprising at least a genipin-crosslinkable functional group, such as amino group. The biological material may be in a form or phase of solution, paste, gel, suspension, colloid or plasma that is fabricatable and that is solidifiable thereafter.

A "biological device" refers to a medical device which is inserted into, or grafted onto, bodily tissue (for example, muscle, tissue, organs, blood vessels, heart tissue and so forth) to remain for a period of time, such as an extended-release drug delivery device, drug-eluting stent, vascular or skin graft, or orthopedic prosthesis, such as bone, ligament, tendon, cartilage, and muscle. The medical device herein can be a pill, a capsule, a gel, a microsphere or the like for the intended drug slow release. The administration of the medical device herein may consist of oral administration, intramuscular injection, transdermal injection, intravenous injection, or inhalation, wherein the medical device may comprise a pharmaceutically acceptable carrier or diluent.

A "microsphere" is herein intended to mean a pharmaceutical composition appropriately sized and shaped, comprising a bioactive agent and a biological carrier that encapsulates the bioactive agent, wherein the biological carrier is crosslinkable with a crosslinking agent.

In particular, the crosslinked collagen-drug device or compound with drug slow release capability may be suitable as anti restenosis agent in treating atherosclerosis and other therapeutic applications. In one aspect of the invention, it is provided a medical device comprising an apparatus having a surface (for example, a coronary stent), a bioactive agent, and solidifiable biological material loaded onto at least a portion of the surface of the apparatus, the solidifiable material containing the bioactive agent, wherein the biological material is thereafter crosslinked with a crosslinking agent. In another aspect, it is provided a medical device, comprising an apparatus having a surface (for example, a coronary stent or heart valve), a bioactive agent, and solidifiable biological material, the biological material being crosslinked with a crosslinking agent, wherein the solidifiable material is thereafter mixed with the bioactive agent and loaded onto at least a portion of the surface of the apparatus.

"Drug" in this invention is meant to broadly refer to a chemical molecule(s), biological molecule(s) or bioactive agent providing a therapeutic, diagnostic, or prophylactic effect in vivo. "Drug" may comprise, but not limited to, synthetic chemicals, biotechnology-derived molecules, herbs, cells, genes, growth factors, health food and/or alternate medicines.

The "biological substance" is herein intended to mean a substance made of drug-containing biological material that is solidifiable upon change of environmental condition(s) and is biocompatible post-crosslinking with a crosslinker, for example, genipin, epoxy compounds, dialdehyde starch, glutaraldehyde, dimethyl adipimidate, or the like.

Preparation and Properties of Genipin

Genipin, shown in FIG. 11, is an iridoid glycoside present in fruits (*Gardenia jasmindides* Ellis). It may be obtained from the parent compound geniposide, which may be isolated from natural sources as described in elsewhere. Genipin, the aglycone of geniposide, may be prepared from the latter by oxidation followed by reduction and hydrolysis or by enzymatic hydrolysis. Alternatively, racemic genipin may be prepared synthetically. Although FIG. 11 shows the natural configuration of genipin, any stereoisomer or mixture of stereoisomers of genipin as shown later may be used as a crosslinking reagent, in accordance with the present invention.

Genipin has a low acute toxicity, with $LD_{50}$ i.v. 382 mg/k in mice. It is therefore much less toxic than glutaraldehyde and many other commonly used synthetic crosslinking reagents. As described below, genipin is shown to be an effective crosslinking agent for treatment of biological materials intended for in vivo biomedical applications, such as prostheses and other implants, wound dressings, and substitutes.

It is one object of the present invention to provide a drug-collagen-genipin and/or drug-chitosan-genipin compound that is loaded onto the periphery of a cardiovascular stent enabling drug slow-release to the surrounding tissue, to the lumen of the bodily cavity.

Previously, Chang in U.S. Pat. No. 5,929,038 discloses a method for treating hepatitis B viral infection with an iridoid compound of a general formula containing a six-member hydrocarbon ring sharing with one common bondage of a five-member hydrocarbon ring. Further, Moon et al. in U.S. Pat. No. 6,162,826 and No. 6,262,083 discloses genipin derivatives having anti hepatitis B virus activity and liver protection activity. All of which three aforementioned patents are incorporated herein by reference. The teachings of these patents do not disclose preparing tissue/device with scaffolds or collagen matrix with desirable porosity for use in tissue engineering, wherein the raw material source for tissue engineering is chemically modified by genipin, genipin derivatives or its analog with acceptably minimal cytotoxicity.

The genipin derivatives and/or genipin analog may have the following chemical formulas (Formula 1 to Formula 4):

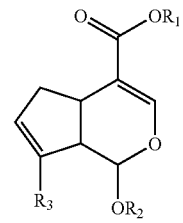

(Genipin Analog Formula 1)

in which $R_1$ represents lower alkyl;

$R_2$ represents lower alkyl, pyridylcarbonyl, benzyl or benzoyl;

$R_3$ represents formyl, hydroxymethyl, azidomethyl, 1-hydroxyethyl, acetyl, methyl, hydroxy, pyridylcarbonyl, cyclopropyl, aminomethyl substituted or unsubstituted by (1,3-benzodioxolan-5-yl)carbonyl or 3,4,5-tri-methoxybenzoyl, 1,3-benzodioxolan-5-yl, ureidomethyl substituted or unsubstituted by 3,4,5-trimethoxyphenyl or 2-chloro-6-methyl-3-pyridyl, thiomethyl substituted or unsubstituted by acetyl or 2-acetylamino-2-ethoxycarbonyethyl, oxymethyl substituted or unsubstituted by benzoyl, pyridylcarbonyl or 3,4,5-trimethoxybenzoyl;

provided that $R_3$ is not methyl formyl, hydroxymethyl, acetyl, methylaminomethyl, acetylthiomethyl, benzoyloxymethyl or pyridylcarbonyloxymethyl when $R_1$ is methyl, and its pharmaceutically acceptable salts, or stereoisomers.

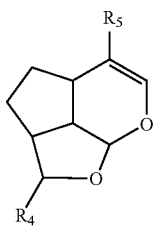

(Genipin Analog Formula 2)

in which $R_4$ represents lower alkoxy, benzyloxy, benzoyloxy, phenylthio, $C_1~C_{12}$ alkanyloxy substituted or unsubstituted by t-butyl, phenyl, phenoxy, pyridyl or thienyl;

$R_5$ represents methoxycarbonyl, formyl, hydroxyiminomethyl, methoxyimino-methyl, hydroxymethyl, phenylthiomethyl or acetylthiomethyl;

provided that $R_5$ is not methoxycarbonyl when $R_{14}$ is acetyloxy; and its pharmaceutically acceptable salts, or stereoisomers.

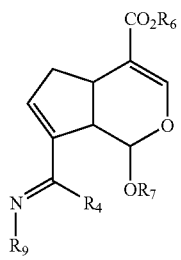

(Genipin Analog Formula 3)

$R_6$ represents hydrogen atom, lower alkyl or alkali metal;
$R_7$ represents lower alkyl or benzyl;
$R_8$ represents hydrogen atom or lower alkyl;
$R_9$ represents hydroxy, lower alkoxy, benzyloxy, nicotinoyloxy, isonicotinoyloxy, 2-pyridylmethoxy or hydroxycarbonylmethoxy;

provided that $R_9$ is not hydroxy or methoxy when $R_6$ is methyl and $R_8$ is hydrogen atom; and its pharmaceutically acceptable salts, or stereoisomers.

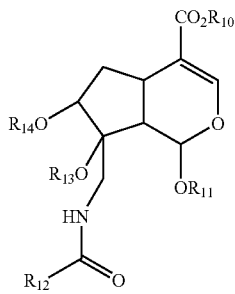

(Genipin Analog Formula 4)

in which $R_{10}$ represents lower alkyl;
$R_{11}$ represents lower alkyl or benzyl;
$R_{12}$ represents lower alkyl, pyridyl substituted or unsubstituted by halogen, pyridylamino substituted or unsubstituted by lower alkyl or halogen, 1,3-benzodioxolanyl;
$R_{13}$ and $R_{14}$ each independently represent a hydrogen atom or join together to form isopropylidene; and its pharmaceutically acceptable salts, or stereoisomers.

Gelatin Microspheres

Gelatin, a polymer from natural sources, is biodegradable, biocompatible, non-toxic, and non-carcinogenic (J Microencapsulation 1998; 15:273-281; and J Microencapsulation 1998; 15:163-172). Gelatin microspheres have been widely evaluated as a drug carrier (J Biomater Sci Polymer Edn 1999; 10:79-94; J Pharm Pharmacol 1981; 33:561-564; and Pharm Res 1989; 6:517-520). Nevertheless, gelatin dissolves rather rapidly in aqueous environments, making the use of the gelatin difficult for the production of long-term delivery systems (Biomaterials 1996; 17:2009-2020; and J Pharm Pharmacol 1984; 36:431-436). This adverse aspect requires the use of crosslinking procedures by formaldehyde or glutaraldehyde, reducing gelatin dissolution and drug release at body temperature by the formation of non-soluble networks in microspheres (it J Pharm 1997; 155:75-82; and Biomaterials 1991; 12:640-644).

Microencapsulation of drugs such as doxorubicin hydrochloride, mitomycin C, and 5-fluorouracil, etc. within the aldehyde-crosslinked gelatin microspheres have been investigated (Int J Pharm 1997; 155:75-82; Biomaterials 1991; 12:640-644; and J Biomater Sci Polymer Edn 1995; 7:623-645). Studies reported in the literature have shown that the aldehyde-crosslinked gelatin microspheres have a long-acting biodegradable ability suitable for controlled-delivery of many drugs (J Biomater Sci Polymer Edn 1995; 7:623-645; and Biomaterials 1994; 15:931-936). However, the use of crosslinkers such as formaldehyde or glutaraldehyde can lead to toxic side effects owing to the residual crosslinking agent. This may impair the biocompatibility of crosslinked products (Biomaterials 1996; 17:2009-2020; Biochimica et Biophysica Acta 1980; 632:589-597; and J Biomed Mater Res 1984; 18:727-736). In an attempt to overcome this problem, a naturally occurring crosslinking agent (genipin) was disclosed to crosslink gelatin microspheres.

Genipin can be obtained from its parent compound, geniposide, which may be isolated from the fruits of Gardenia jasminoides ELLIS. Genipin and its related iridoid glucosides have been widely used as an antiphlogistic and cholagogue in herbal medicine (Biol Pharm Bull 4; 17:1573-1576). Additionally, it was reported that genipin can spontaneously react with amino acids or proteins to form dark blue pigments (Chem Pharm Bull 1994; 42:668-673; and Chem Pharm Bull 1994; 42:1571-1578). These dark blue pigments have been used in the fabrication of food dyes. It was found in our previous study that genipin could react with the free amino groups of lysine, hydroxylysine, or arginine residues within collagen-based biomaterials (J Biomed Mater Res 1998; 42:560-67).

The feasibility of using genipin to crosslink gelatin as a novel biological glue to close skin-wound lesions has been previously evaluated in vitro and in vivo in a rat model (J Biomed Mater Res 1999; 46:520-530; and J Biomater Sci Polymer Edn 1999; 10:751-771). Formaldehyde and glutaraldehyde were used as controls. The results showed that the cytotoxicity of the genipin-crosslinked glue was significantly less than the aldehyde-crosslinked glues. Additionally, in the animal study, it was found that the wounds treated by the genipin-crosslinked glue induced significantly less inflammatory responses and recovered sooner than those treated by the aldehyde-crosslinked glues.

The disclosed study was intended to illustrate the feasibility of using genipin to crosslink gelatin microspheres as a biodegradable drug-delivery system for intramuscular administration and other medical applications. The glutaraldehyde-crosslinked counterparts were used as a control. In the in intro study, the morphology, dynamic swelling, and anti-enzymatic degradation of test microspheres were evaluated. In the in vivo study, the biocompatability and degradability (that is, durability) of test microspheres were investigated in a rat model.

EXAMPLE #1

Preparation of Gelatin Microspheres

Gelatin microspheres were prepared using the emulsification-solvent-extraction method reported in the literature with some modifications (J Microencapsulation 1998; 15:273-281; and J Pharm Sci 1963; 52:664-667). Briefly speaking, gelatin (2.5 g, from porcine skin, 300 Bloom, Sigma Chemical Co., St. Louis, Mo., USA) was dissolved in 10 mL phosphate-buffered saline (PBS, pH 7.4) in a water bath at 50° C. The gelatin solution was added to a 50-mL corn oil and preheated to 50° C. The biphasic system (corn oil and aqueous solution containing gelatin) was thoroughly mixed to form a w/o emulsion using a magnetic mixer for 20 min. Subsequently, the emulsion system was chilled to 4° C. in a refrigerator and gelatin microspheres were formed in the aqueous phase. The gelatin microspheres then were rinsed in acetone for several times to remove the remaining oil on their surfaces. Finally, the rinsed gelatin microspheres were vacuum-dried overnight. The particle-size of gelatin microspheres was measured by a light-scattering particle-size analyzer (Galai, CIS-1). In one aspect of the invention, drug or other pharmaceutical agents can be added in the emulsion system to yield a drug-containing gelatin microsphere. The gelatin microspheres can also be manufactured by spray drying processes.

Some aspects of the invention relate to genipin-crosslinked gelatin as a drug carrier. In one embodiment, it is provided a method for treating tissue of a patient comprising, in combination, loading a solidifiable drug-containing gelatin onto an apparatus or medical device, solidifying the drug-containing gelatin, chemically treating the gelatin with a crosslinking agent, and delivering the medical device to the tissue for treating the tissue. Gelatin microspheres haven been widely evaluated as a drug carrier. However, gelatin dissolves rather rapidly in aqueous environments, making the use of gelatin difficult for the production of long-term drug delivery systems. Hsing and associates reported the degradation rate of the genipin-crosslinked microspheres is significantly increased (J Biomed Mater Res 2003; 65A:271-282).

Some aspects of the invention provide a pharmaceutical microsphere, comprising: a bioactive agent; and a biological carrier that encapsulates the bioactive agent, wherein the biological carrier is crosslinked with a crosslinking agent. Further, some aspects of the invention provide a method for administering a pharmaceutical microsphere or microspheres into a body of a patient comprising: providing the pharmaceutical microsphere(s) that comprises a bioactive agent and a biological carrier, the biological carrier encapsulating the bioactive agent, wherein the biological carrier is crosslinked with a crosslinking agent; and delivering or introducing the pharmaceutical microsphere(s) into the body for therapeutic treatment. In one embodiment, the method further comprises a step of loading the pharmaceutical microsphere(s) onto a medical device before the delivering step, wherein the medical device is a stent, a non-stent implant, a device selected from a group consisting of annuloplasty rings, heart valve prostheses, venous valve bioprostheses, orthopedic implants, dental implants, opthalmology implants, cardiovascular implants, and cerebral implants, or a percutaneous apparatus selected from a group consisting of a catheter, a wire, a cannula, and an endoscopic instrument.

EXAMPLE #2

Crosslinking of Gelatin Microspheres

The prepared gelatin microspheres (0.15 g) from Example #1 were dispersed into a 0.44M genipin (Challenge Bioproducts, Taiwan) or 0.22M glutaraldehyde (Merck KGaA, Darmstadt, Germany) of aqueous ethanol solution (90% ethanol by volume) for crosslinking. The degree of crosslinking, determined by the ninhydrin assay, was defined as the percentage of free amino groups in gelatin microspheres reacted with each test crosslinking agent subsequent to crosslinking. In the ninhydrin assay, the sample first was lyophilized for 24 h and weighed. Subsequently, the lyophilized sample was heated with a ninhydrin solution for 20 min. After heating with ninhydrin, the optical absorbance of the solution was recorded with a spectrophotometer (Model UV-150-02, Shimadzu Corp., Kyoto, Japan) using glycine at various known concentrations as standard. It is known that the amount of free amino groups in the test sample, after heating with ninhydrin, is proportional to the optical absorbance of the solution (Biochemistry, 3rd ed. New York: Freeman, 1988, p. 50-5).

The degrees of crosslinking for both the glutaraldehyde- and genipin-crosslinked gelatin microspheres used in the in vitro and in vivo studies were approximately 60% by adjusting their crosslinking duration for 45 minutes and 72 hours, respectively. The crosslinked gelatin microspheres then were rinsed with aqueous ethanol solution (99.5% ethanol by volume) to remove residual glutaraldehyde or genipin for 4 hours. Subsequently, the rinsed microspheres were vacuum-dried for 24 hours to evaporate ethanol. The crosslinked microspheres were sprinkled onto a double-sided adhesive tape fixed to an aluminum stage. The fixed microspheres were spattered with gold film. Examination of microspheres was performed with a scanning electron microscope (Hitachi, Model S-2300, Japan).

Figure 1:
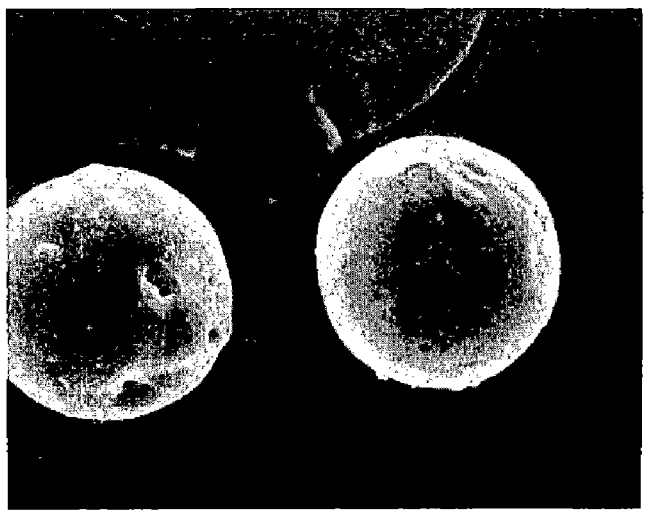
FIG. 1 is SEM micrographs of gelatin microspheres prepared by the emulsification-solvent-extraction method. Fresh: before crosslinking; GA: glutaraldehyde-crosslinked; GP: genipin-crosslinked.
Figure 1:
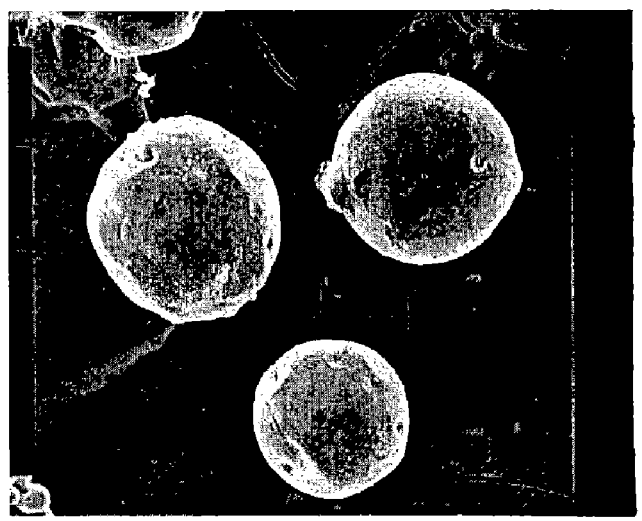
Figure 1:
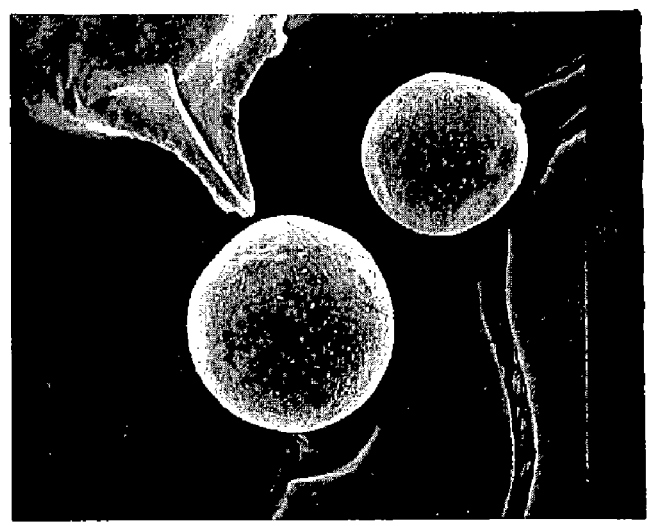

The gelatin microspheres prepared by the emulsification-solvent-extraction method showed a good sphericity (FIG. 1). The particle-size distribution of prepared gelatin microspheres was affected significantly by the process conditions, such as the aqueous gelatin concentration, the rotation speed of the magnetic mixer, and the duration of emulsification. It was found that increasing the aqueous gelatin concentration yielded microspheres with a significant larger particle-size. Additionally, with increase in the rotation speed of the magnetic mixer and the duration of emulsification produced microspheres with a smaller mean particle-size and a narrower size distribution. Crosslinking gelatin microspheres with glutaraldehyde or genipin did not induce a significant change in their morphology (FIG. 1). After crosslinking, the color of the glutaraldehyde-crosslinked gelatin microspheres turned yellowish, while that of the genipin-crosslinked microspheres became dark-bluish.

Figure 2:
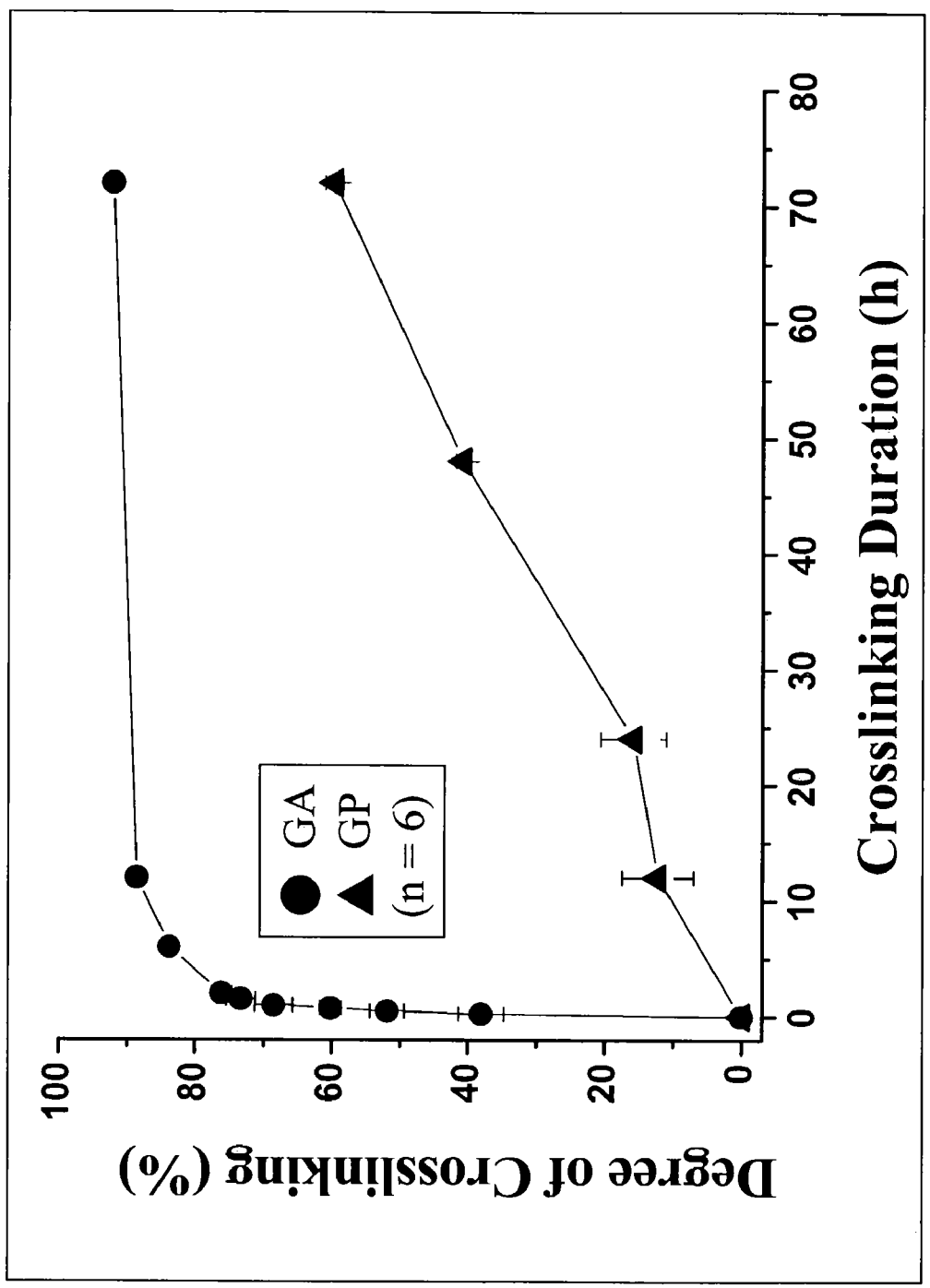
FIG. 2 are degrees of crosslinking for the glutaraldehyde- and genipin-crosslinked microspheres obtained at distinct crosslinking durations.

FIG. 2 shows degrees of crosslinking for the glutaraldehyde (GA)- and genipin (GP)-crosslinked microspheres obtained at distinct crosslinking durations. As shown in the figure, after a 72-hour crosslinking, the highest degree of crosslinking for the genipin-crosslinked microspheres was approximately 60%. Therefore, the degrees of crosslinking for both the glutaraldehyde- and genipin-crosslinked microspheres were set at 60% for the rest of the study.

Dynamic Swelling of Test Microspheres

The dynamic swelling of the glutaraldehyde- and genipin-crosslinked gelatin microspheres was performed as per the method reported by Robert et al. in the literature (J Controlled Release 1987; 5:151-157). Dried test microspheres were placed on the observation plates equipped with liquid containers and studied under an optical microscope (Olympus Optical Co., Ltd., IX70, Tokyo, Japan). Their initial diameter, $d_0$, was recorded and the containers were filled with deionized water. The increase of the swelling diameter, $d_t$, due to water transport in test microspheres was observed as a function of time at room temperature, until microspheres achieved full equilibrium with a diameter $d\infty$. Six microspheres with diameters between 250 and 300 μm were tested for each studied group.

The mechanism of water transport in test microspheres can be analyzed by the examination of the curves of water uptake as a function of time based on the following equation (J Controlled Release 1987; 5:151-157):

$$(d_t-d_0)/d_0=kt^n \qquad \text{(Equation 1)}$$

Here $(d_t-d_0)/d_0$ is the fractional amount of water uptake, t is the water transport time, k is a diffusional kinetic constant, and n is the diffusional exponent. When analyzing transport data for $(d_t-d_0)/d_0<0.6$, the value of the diffusional exponent (n) is a good indication of water transport mechanism (J Controlled Release 1987; 5:151-157; and Pharmazie 1991; 46:866-869).

Figure 3:
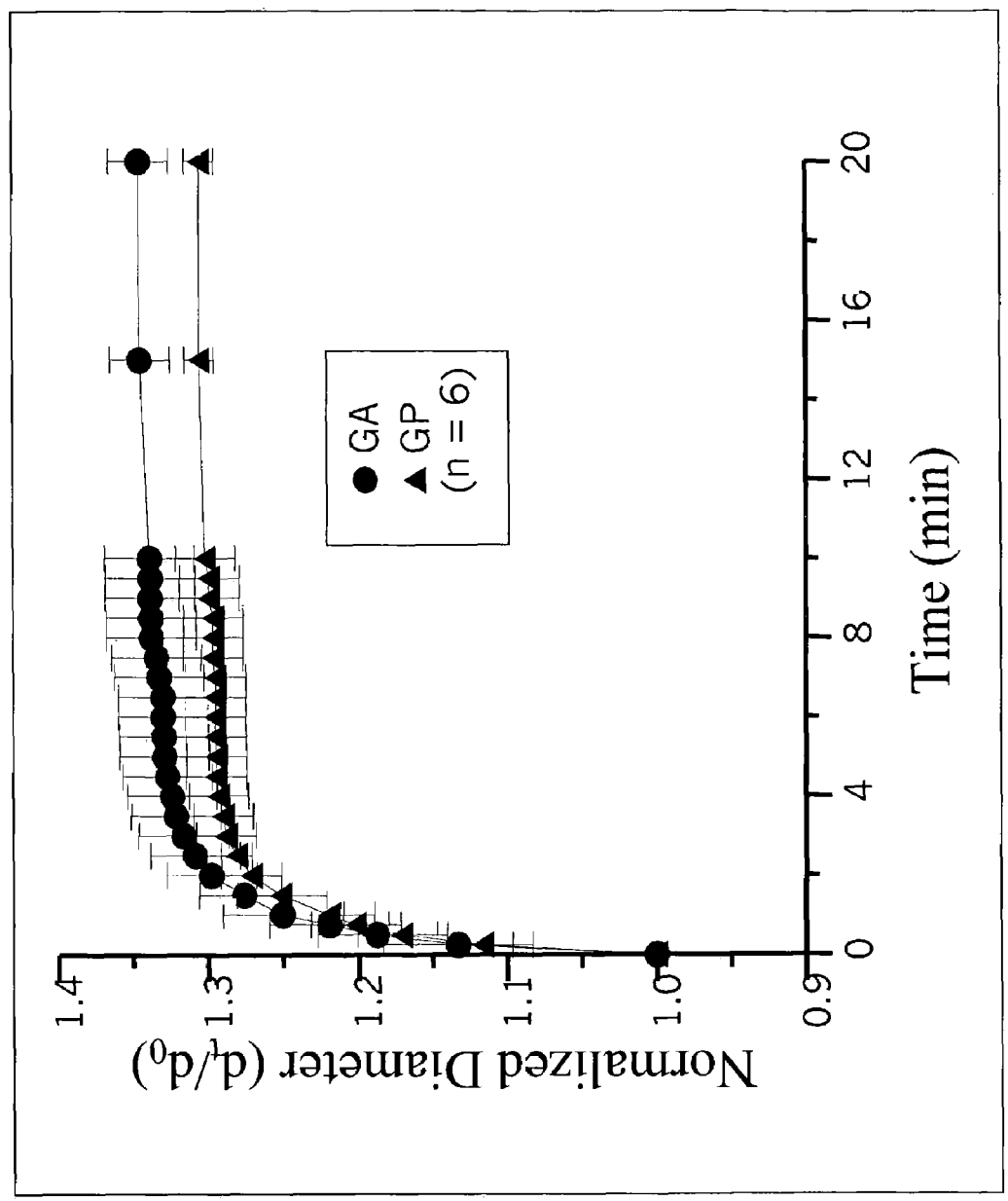
FIG. 3 are changes of the normalized particle-diameter ($d_t/d_0$) with time for the glutaraldehyde- (GA) and genipin-crosslinked (GP) gelatin microspheres.

The dynamic swelling of test microspheres was performed in deionized water at room temperature. FIG. 3 shows changes of the normalized particle-diameter with time for the glutaraldehyde- and genipin-crosslinked gelatin microspheres. As shown in the figure, the normalized particle-diameters for both test microspheres increased remarkably initially (P<0.05) and achieved full equilibrium at approximately 5 minutes after immersing in deionized water. The equilibrium diameter ($d\infty$) of the glutaraldehyde-crosslinked microspheres was significantly greater than the genipin-crosslinked counterparts (P<0.05). The mechanism of water transport in test microspheres can be analyzed by Equation 1. As per the data reported in FIG. 3, the values of the diffusional exponent (n) in Equation 1 for the glutaraldehyde- and genipin-crosslinked gelatin microspheres were 0.59 and 0.49 ($r^2$=0.99), respectively.

In Vitro Enzymatic Degradation of Test Microspheres

Enzymatic degradation of the glutaraldehyde- and genipin-crosslinked gelatin microspheres was performed using collagenase (*Clostridium histolyticum*, EC 3.4.24.3, P/N C-0130, Sigma Chemical Co.) with an activity of 315 U/mg solid. Degradation of test microspheres without collagenase was used as a control. Test microspheres ($W_1$) were well immersed in a 20 U/mL collagenase solution (pH 7.5) and incubated at 37° C. for 24 hours. Degradation of test microspheres was discontinued at the desired duration by adding a 10 mM EDTA (ethylenediaminetetraactic acid, Sigma #E9884) solution. The morphology of test microspheres after enzymatic degradation was grossly examined using a scanning electron microscope as described above. Additionally, the weight loss of test microspheres due to degradation with or without collagenase was quantified as follows:

$$\text{Weight loss}(\%)=(W_1-W_2)/W_2\times100 \qquad \text{(Equation 2)}$$

Where, $W_2$ is the weight of degraded test microspheres lyophilized for 24 hours.

Representative SEM micrographs for the glutaraldehyde- and genipin-crosslinked gelatin microspheres at 1-day after degradation with or without collagenase are shown in FIG. 4A and FIG. 4B. After degradation, it was found that the degrees in degradation, with or without collagenase, for the glutaraldehyde-crosslinked gelatin microspheres were more remarkable than the genipin-crosslinked microspheres. The weight losses measured for the glutaraldehyde-crosslinked microspheres (41.3±3.0% with collagenase degradation, 12.0±1.2% without collagenase degradation) were significantly greater than the genipin-crosslinked microspheres (20.2±2.0% with collagenase degradation, 7.9±0.9% without collagenase degradation, n=6, P<0.05).

EXAMPLE #3

Animal Study

The in vivo biocompatibility and degradability of the glutaraldehyde- and genipin-crosslinked gelatin microspheres were examined by implanting test microspheres in the skeletal muscle of the thigh via intramuscular injection in a rat model (Wistar). The test microspheres were sterilized in a 95% ethanol solution over a period of 4 hours. The sterilized microspheres (~80 μm size), 50 mg, were suspended in 2 mL of physiological saline and injected into the skeletal muscle using an 18G needle. Each animal received two injections (one for the glutaraldehyde-crosslinked microspheres and the other for the genipin-crosslinked microspheres) on either side of the skeletal muscle. The implanted microspheres along with their surrounding tissues were respectively retrieved at 3-day, 1-week, 2-week, 3-week, and 4-week postoperatively. On retrieval, the appearance of each retrieved sample first was grossly examined and photographed. The samples then were processed for histological and scanning election microscopic (SEM) examinations.

The retrieved samples used for the histological examination were fixed in a 10% phosphate-buffered formaldehyde solution for at least 3 days. The fixed samples were embedded in paraffin, sectioned into a thickness of 5 μm, and then stained with hematoxylin and eosin (H&E). The stained sections of each test sample were examined using light microscopy (Nikon Microphoto-FXA) for tissue inflammatory reaction and photographed with a 100 ASA Kodachrome film. The number of inflammatory cells observed in each studied case was quantified with a computer-based image analysis system (Image-Pro® Plus, Media Cybernetics, Silver Spring, Md., USA). Inflammatory cells were visually identified (200× magnification) and the number was counted for each microscopic field (J Biomed Mater Res 2001; 55:576-86). A minimum of five fields was counted for each retrieved sample.

The samples used for the SEM examination first were fixed with 2% glutaraldehyde in 0.1M of sodium cacodylate and then post-fixed in 1% osmium tetroxide. Subsequently, the samples were dehydrated in a graded series of ethanol solutions, critical-point dried with carbon dioxide, and spattered with gold film. The examination was performed with a scanning electron microscope (Hitachi S-2300).

Figure 5:
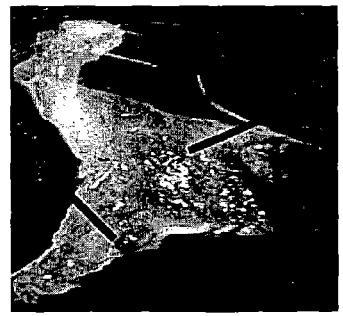
FIG. 5 are photographs of implanted test microspheres along with their surrounding tissues retrieved at distinct postoperative durations. GA: the glutaraldehyde-crosslinked microspheres; GP: the genipin-crosslinked microspheres.
Figure 5:
Figure 5:
Figure 5:
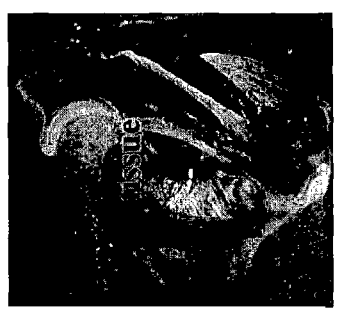
Figure 5:
Figure 5:
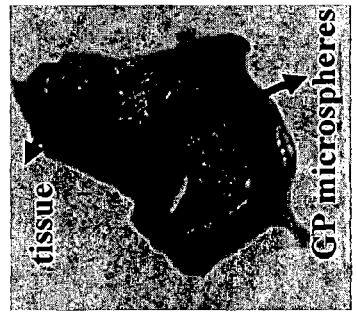
Figure 5:
Figure 5:
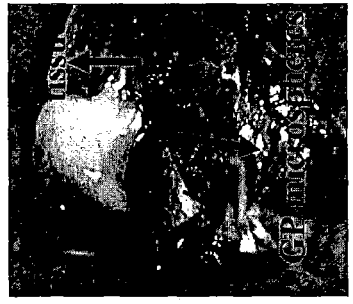
Figure 5:
Figure 5:

On retrieval, the implanted test microspheres along with their surrounding tissues retrieved at distinct postoperative durations were grossly examined and photographed (FIG. 5). As shown in the figure, both the glutaraldehyde-crosslinked microspheres (yellowish color) and the genipin-crosslinked microspheres (dark-bluish color) were disintegrated progressively with time and finally disappeared. It was noted that the glutaraldehyde-crosslinked microspheres had started to disappear at approximately 14-day after implantation. No glutaraldehyde-crosslinked microspheres were observed at 21-day postoperatively. In contrast, there were still a few genipin-crosslinked microspheres remaining in the tissue at 28-day postoperatively. This observation indicated that the rate of degradation for the genipin-crosslinked gelatin microspheres was significantly slower than the glutaraldehyde-crosslinked microspheres.

Figure 6:
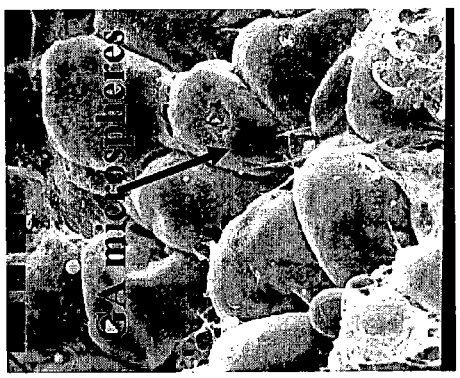
FIG. 6 are SEM micrographs of tissues implanted with the glutaraldehyde-(GA) and genipin-crosslinked (GP) gelatin microspheres retrieved at distinct durations postoperatively.
Figure 6:
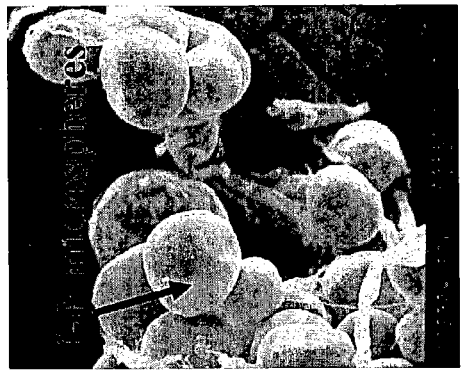
Figure 6:
Figure 6:
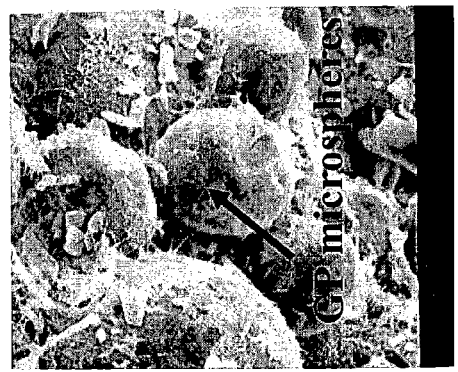
Figure 6:
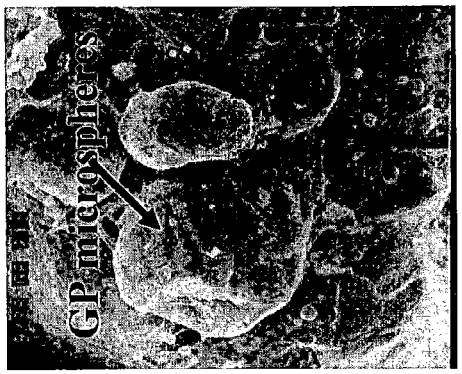

FIG. 6 shows SEM micrographs of the implanted test microspheres retrieved at distinct durations after implantation. At 3-day postoperatively, both the glutaraldehyde- and genipin-crosslinked microspheres remained in a good sphericity as those observed before implantation. However, the morphology of the implanted test microspheres became concave on their surfaces progressively with time. It was noted that the surfaces for the majority of the glutaraldehyde-crosslinked microspheres already became concave at 14-day postoperatively. In contrast, the morphology of the genipin-crosslinked microspheres still remained in a good sphericity until at 21-day postoperatively. It is an embodiment of the present invention to provide a gelatin sphere in a generally spherical configuration. However, in a further embodiment, any shape, spherical or generally non-spherical gelatin microspheres, is within the scope of the present invention.

Figure 7:
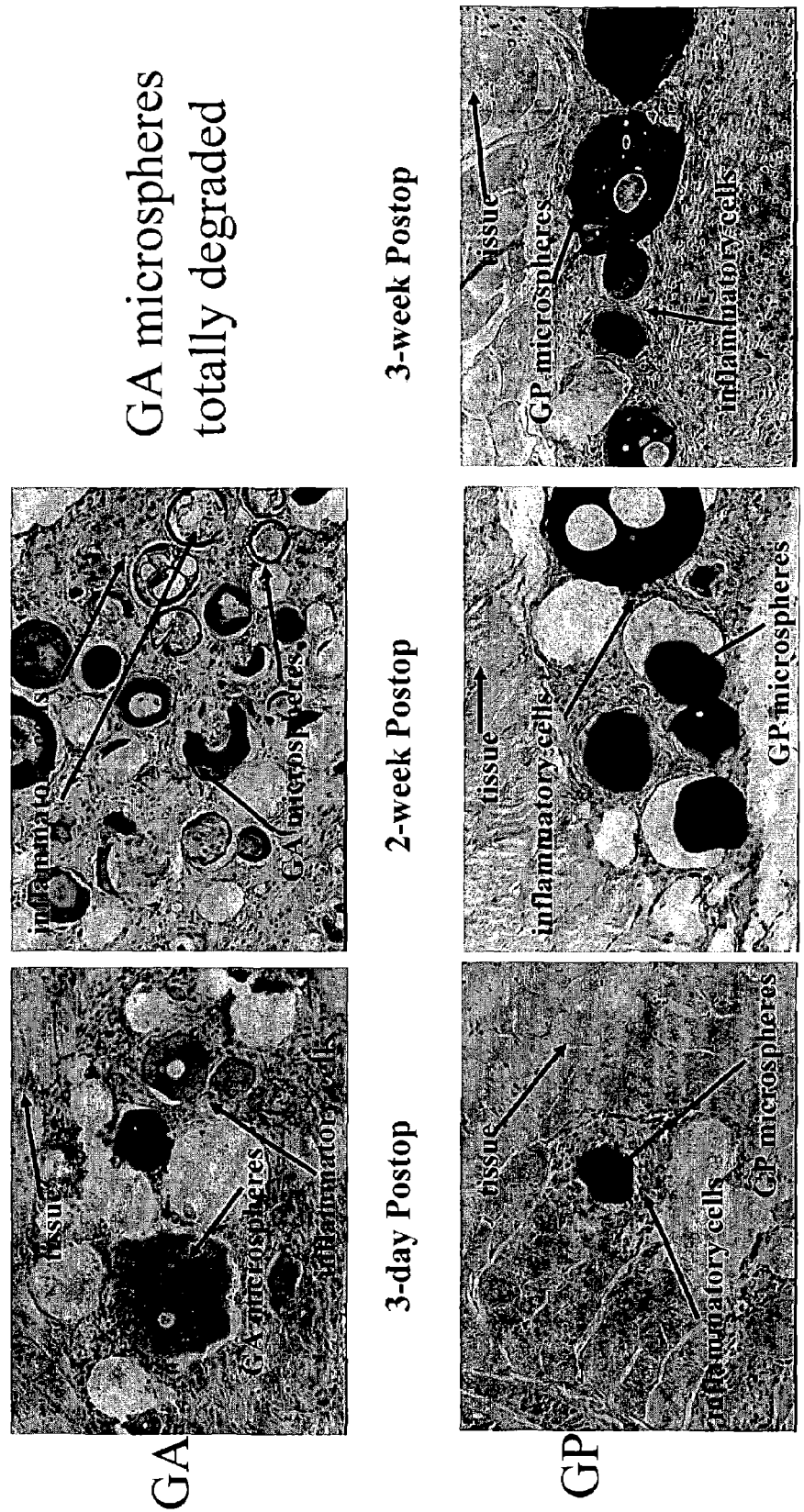
FIG. 7 are photomicrographs of tissues implanted with the glutaraldehyde-(GA) and genipin-crosslinked (GP) gelatin microspheres stained with H&E (200× magnification) retrieved at distinct durations postoperatively.
Figure 8:
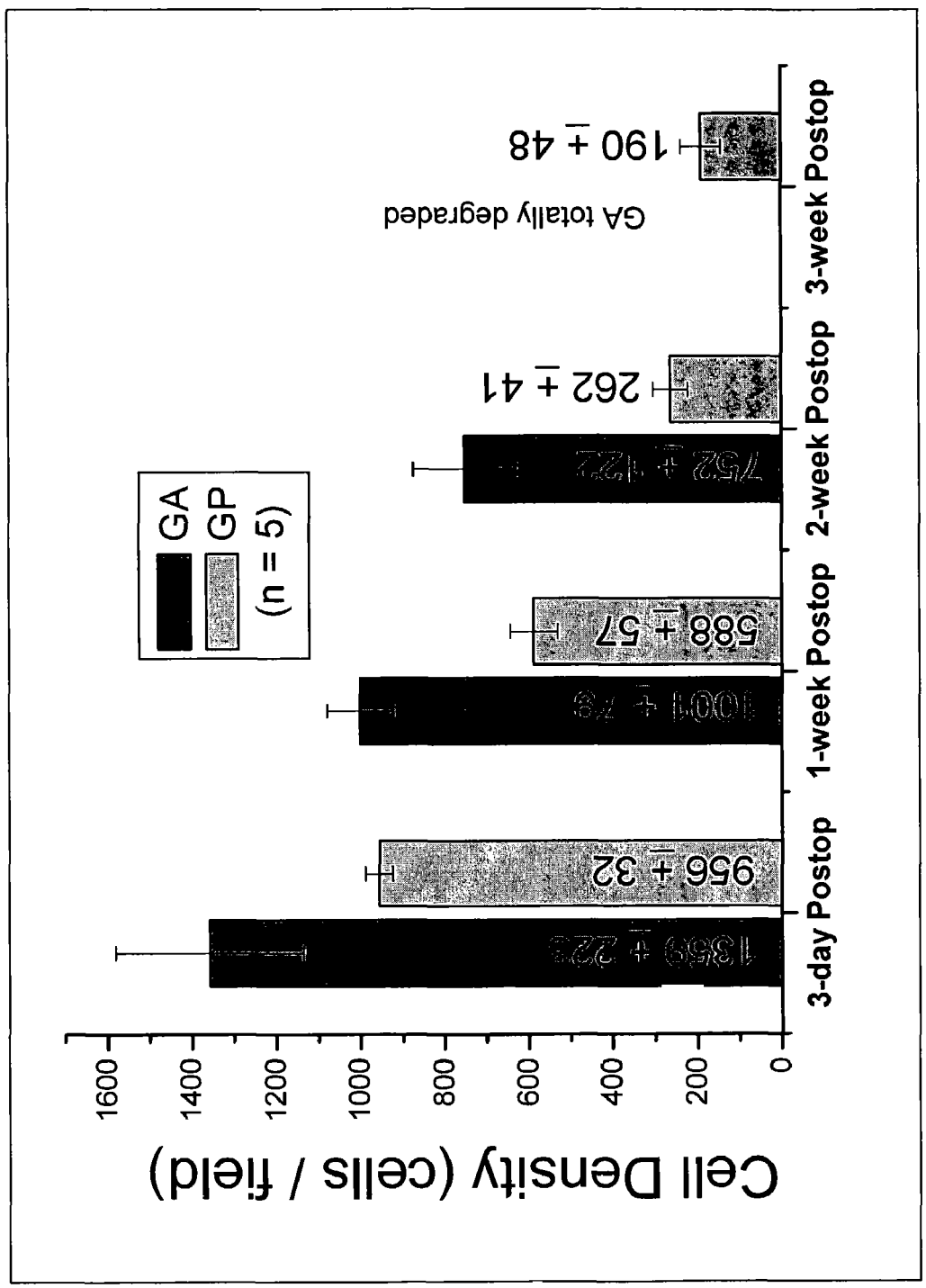
FIG. 8 are densities of inflammatory cells observed for tissues implanted with the glutaraldehyde- (GA) and genipin-crosslinked (GP) gelatin microspheres retrieved at distinct durations postoperatively.

FIG. 7 shows photomicrographs of tissues implanted with the glutaraldehyde- and genipin-crosslinked gelatin microspheres stained with H&E retrieved at distinct durations postoperatively. Additionally, the numbers of inflammatory cells observed in tissues surrounding test microspheres were quantified with a computer-based image analysis system (FIG. 8). At 3- and 7-day after implantation, the degrees of inflammatory reaction observed for tissues implanted with the glutaraldehyde-crosslinked microspheres were significantly greater than the genipin-crosslinked microspheres (FIG. 8, $P<0.05$). At these moments, the inflammatory cells observed in tissues were mainly surrounding the implanted microspheres for both studied cases.

At 14-day postoperatively, the degree of inflammatory reaction for tissue implanted with the genipin-crosslinked microspheres declined significantly ($P<0.05$). However, the inflammatory cells observed in tissue implanted with the glutaraldehyde-crosslinked microspheres were still abundant, suggesting that the inflammatory reaction persisted for this case. Of note is that the structure of the glutaraldehyde-crosslinked microspheres already became porous. Due to disintegration of the glutaraldehyde-crosslinked microspheres, the inflammatory cells were able to infiltrate into the implanted microspheres. In contrast, the structure of the genipin-crosslinked microspheres still remained in a good sphericity until at 21-week postoperatively.

Statistical analysis for the determination of differences in the measured properties between groups was accomplished using one-way analysis of variance and determination of confidence intervals, performed with a computer statistical program (Statistical Analysis System, Version 6.08, SAS Institute Inc., Cary, N.C., USA). All data are presented as a mean value with its standard deviation indicated (mean ±SD).

Characteristics of Gelatin Microspheres

The simple and complex coacervation (J Pharm Sci 1974; 63:409-411), emulsification-solvent-extraction (J Pharm Sci 1963; 52:664-667; Drug Dev Ind Pharm 1990; 16:1025-1051), and adsorption (J Microencapsulation 1994; 11:69-77) methods have been used in the preparation of gelatin microspheres for drug carrier. Among these methods, it was reported that the emulsification-solvent-extraction method, initially proposed by Tanaka et al. (J Pharm Sci 1963; 52:664-667), is the simplest. The emulsification-solvent-extraction method has been widely used in the microencapsulation of both water-soluble and insoluble drugs (J Pharm Sci 1967; 9:1174-1177). In the study, preparation of gelatin microspheres was based on the emulsification-solvent-extraction method reported in the literature with some modifications (J Microencapsulation 1998; 15:273-281; and J Pharm Sci 1963; 52:664-667).

It was found that the duration of emulsification and the rotation speed of the magnetic mixer are critical factors in affecting the particle-size of gelatin microspheres. The longer duration of emulsification and the greater speed of the magnetic mixer, the smaller the particle-size of gelatin microspheres is. Additionally, the viscosity of the gelatin solution (or the gelatin concentration in the aqueous phase) has a great effect on the droplet-size of emulsion and consequently on the microsphere size. It was noted that the greater the viscosity of the gelatin solution, the larger the aqueous droplet in emulsion is, and consequently the larger the gelatin microspheres.

It was reported that microspheres with a diameter in the range of 20~100 μm can be used for intramuscular administration (Biomaterials 1996; 17:2009-2020). Microspheres with a diameter in this specific range are retained in the interstitial tissue acting as sustained release depots (Biomaterials 1996; 17:2009-2020; and Biomaterials 1991; 12:640-644). With the emulsification-solvent-extraction method reported in the study, the process conditions that can produce gelatin microspheres with a diameter between 20 and 100 μm were: a gelatin concentration of 250 mg/mL, an emulsification duration of 20 min, and a volume ratio of gelatin solution to oil phase of 0.2. Under these conditions, the gelatin microspheres made in the study had an average particle-size of 82 μm. No particle aggregation or fusion was observed during the process.

Figure 9A:
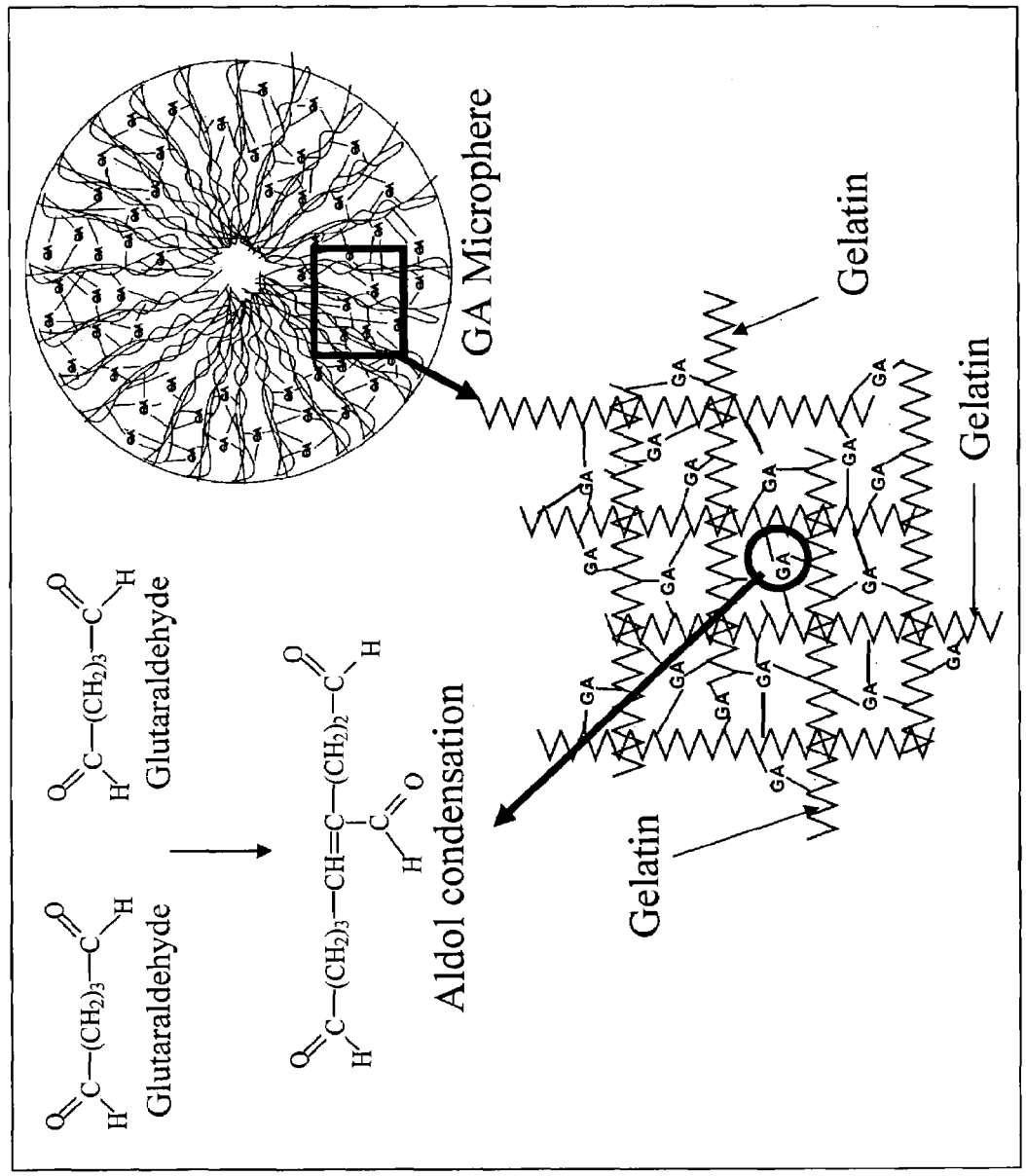
FIGS. 9A and 9B are schematic illustrations of the presumable crosslinking structures for (a) the glutaraldehyde-crosslinked gelatin microspheres and (b) the genipin-crosslinked gelatin microspheres. GA: glutaraldehyde; GP: genipin.

Glutaraldehyde has been used extensively as a crosslinking agent for crosslinking collage-based biomaterials (J Biomed Mater Res 1980; 14:753-764). Using its aldehyde functional groups, glutaraldehyde reacts primarily with the ε-amino groups of lysyl or hydroxylysyl residues within collagen-based biomaterials. Polymerization of glutaraldehyde molecules in aqueous solution with observable reductions in free aldehyde has been reported previously (Nimni M E, editor. Collagen, Vol. III. Boca Raton, Fla.: CRC Press, 1988: p. 1-38; J R Microsc Soc 1966; 85:193-200). In polymerization, the aldehyde functional groups of two glutaraldehyde molecules may undergo an aldol condensation as shown in FIG. 9A (Nimni M E, editor. Collagen, Vol. III. Boca Raton, Fla.: CRC Press, 1988: p. 1-38). With glutaraldehyde polymerization, subsequent to crosslinking, a network crosslinking structure can be created intramolecularly and intermolecularly within collagen-based biomaterials as shown in FIG. 9A. The mechanism of crosslinking of collagen-based biomaterials with glutaraldehyde can be found in the literature (Nimni M E, editor. Collagen, Vol. 111. Boca Raton, Fla.: CRC Press, 1988: p. 1-38; Biomaterials 1996; 17:471-84).

Figure 9B:
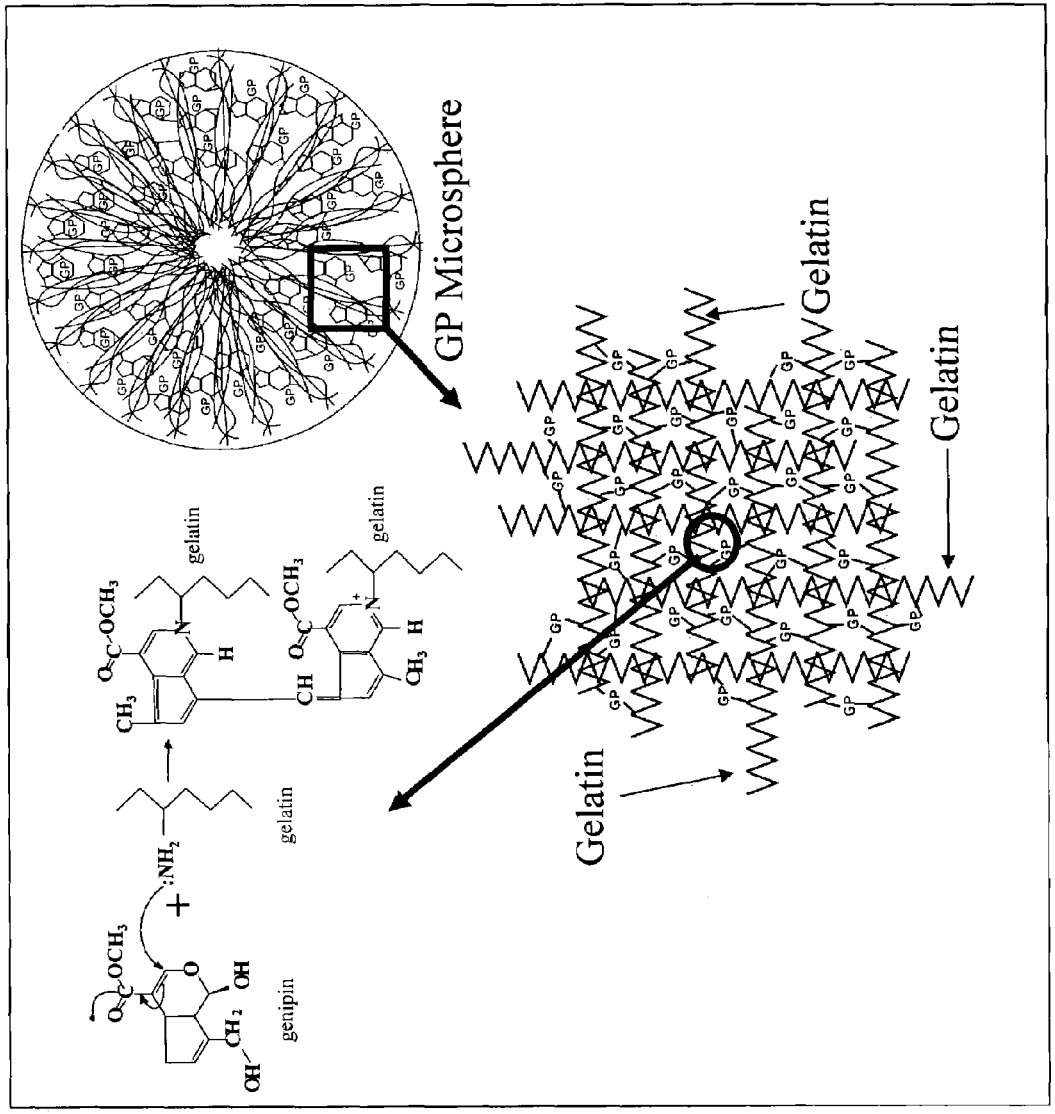

The dark bluish color observed with the genipin-crosslinked microspheres was a result of the reaction of genipin with the amino acid residues in gelatin molecules. The reaction mechanism of amino-group-containing compounds with genipin has been discussed in the literature (Chem Pharm Bull 1994; 42:668-673; and Chem Pharm Bull 1994; 42:1571-1578). It was proposed that a genipin-amino-group monomer is formed though a nucleophilic attack by the amino-group-containing compounds such as gelatin on the third carbon of genipin. This follows by the opening of the genipin ring and forms an aldehyde group. Subsequently, the resulting aldehyde group is attacked by the attached secondary amino group. Dimerization occurs at the second stage, perhaps by radical reaction. Therefore, genipin may form intramolecularly and intermolecularly crosslinked products with a heterocyclic structure (FIG. 9B).

Figure 10:
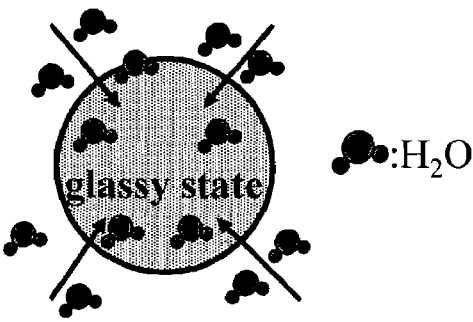
FIG. 10 are schematic illustrations of varying models for water transport in test microspheres.
Figure 10:
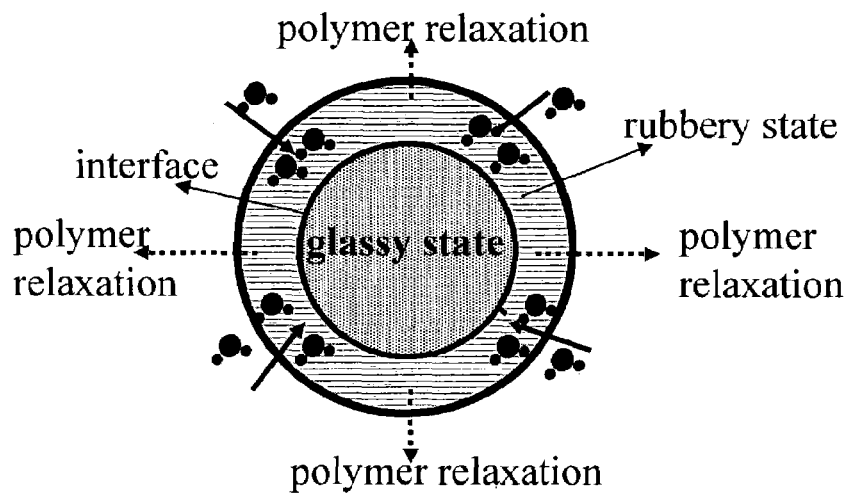
Figure 10:
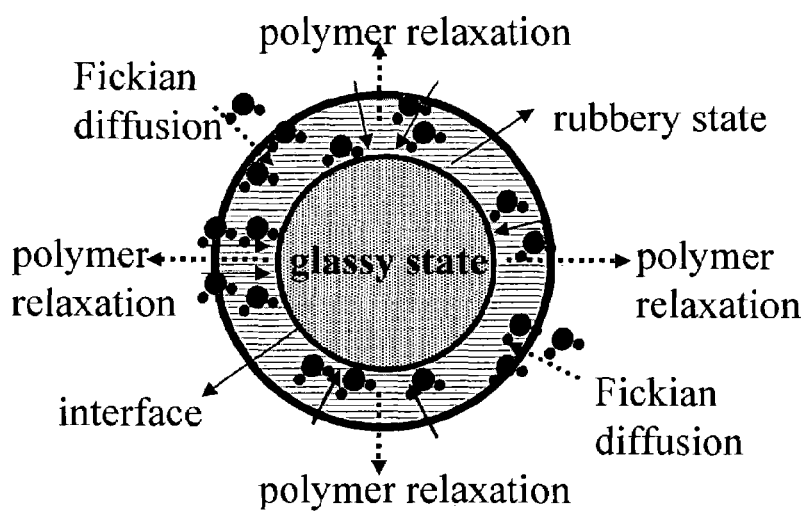

It was reported that the value of the diffusional exponent (n) in Equation 1 is a good indication of the water transport mechanism in test microspheres, when analyzing data for $(d_t-d_0)/d_0 \leq 0.6$. (J Controlled Release 1987; 5:151-157; and Pharmazie 1991; 46:866-869). For n=0.43 and n=0.85 in Equation 1, the water transport mechanisms in test microspheres are Fickian diffusion and Case-II transport, respectively (FIG. 10). The water transport mechanism in test microspheres in the Fickian-diffusion model (glassy state) is primarily diffusion-controlled. Typically, for a polymer slab, Fickian diffusion is characterized by a square-root time dependence in the position of the penetrating diffusion front (J Control Rel 1985; 2:277-288). In contrast, the water transport mechanism in the Case-II model is mainly due to the relaxation of polymer chains in test microspheres accompanied by a considerable volume expansion in a rubbery state (J Control Rel 1985; 2:277-288).

For values of n between these two limits, the water transport mechanism in test microspheres is termed anomalous (FIG. 10). This intermediate situation will exist whenever the rates of Fickian diffusion and polymer relaxation are comparable. It was noted that the values of the diffusional exponent (n) in Equation 1 for the glutaraldehyde- and genipin-crosslinked gelatin microspheres were between 0.43 and 0.85. As a result, the water transport mechanisms in both the glutaraldehyde- and genipin-crosslinked gelatin microspheres exhibit anomalous behavior ranging from Fickian to Case-II extremes (FIG. 10). The particle-diameters of both test microspheres increased remarkably due to polymer relaxation after immersing in deionized water (FIG. 3).

The heterocyclic crosslinking structure of the genipin-crosslinked microspheres appeared to be relatively more difficult in relaxation than the network crosslinking structure of the glutaraldehyde-crosslinked microspheres, because of its bulky heterocyclic structure present (FIG. 9). Therefore, the particle-diameter at equilibrium (d∞) for the genipin-crosslinked microspheres was significantly smaller than that observed for the glutaraldehyde-crosslinked microspheres (FIG. 3). Additionally, the value of the diffusional exponent (n) in Equation 1 for the genipin-crosslinked microspheres (n=0.49) was smaller than the glutaraldehyde-crosslinked microspheres (n=0.59). This implied that the anomalous behavior for water transport in the genipin-crosslinked microspheres is closer to the Fickian-diffusion extreme than the glutaraldehyde-crosslinked counterparts, due to their heterocyclic crosslinking structure more difficult in relaxation.

The in vivo biocompatibility of the glutaraldehyde- and genipin-crosslinked gelatin microspheres was assessed in a rat model via intramuscular injection. It was noted that the degree in inflammatory reaction for tissue implanted with the genipin-crosslinked microspheres was significantly less than its glutaraldehyde-crosslinked counterparts (FIG. 8). This observation implied that the biocompatibility of the genipin-crosslinked microspheres is superior to the glutaraldehyde-crosslinked microspheres. A disadvantage of the chemically modified implants is the potential toxic effects a recipient may be exposed to from its remaining residues. It is speculated that the less inflammatory reaction observed for the genipin-crosslinked microspheres may be due to the lower toxicity of their remaining residues as compared to the glutaraldehyde-crosslinked microspheres. It was observed in our previous study that the cytotoxicity of genipin is significantly lower than glutaraldehyde (J Biomater Sci Polymer Edn 1999; 10:63-78).

Bacterial collagenase from *Clostridium histolyticum* was selected as the enzyme for our in vitro degradation study. It was reported that bacterial collagenase, a specific protease, splits tropocollagen molecules into small fragments between X and Gly in the Pro-X-Gly-Pro-Y sequence (Nimni M E, editor. Collagen, Vol. I. Boca Raton, Fla.: CRC Press; 1988. pp. 1-77). The weight loss with collagenase degradation was significantly greater than that without collagenase degradation for both the glutaraldehyde- and genipin-crosslinked microspheres. The SEM micrographs shown in FIGS. 4A and 4B indicated that the degrees in degradation, with or without collagenase, for the glutaraldehyde-crosslinked gelatin microspheres were more remarkable than the genipin-crosslinked microspheres. Additionally, the weight losses measured for the glutaraldehyde-crosslinked microspheres were significantly greater than their genipin-crosslinked counterparts.

Similar results were observed in the animal study, at 14-day postoperatively, the structure of the glutaraldehyde-crosslinked microspheres already became porous. In contrast, the structure of the genipin-crosslinked microspheres still remained in a good sphericity until at 21-week postoperatively (FIG. 7). Clinically, degradation of the implanted biomaterials may be induced by the host inflammatory reaction. Previous studies have shown that implanted biomaterials provoke a cellular response that leads to physical invasion of the implants by various inflammatory cells such as polymorphonuclear leukocytes and macrophages and fibroblasts (Brit J Urol 1986; 58:203-207; and Biomaterials 1990; 11:113-118). Macrophages are known to be able to secrete collagenase among other proteases (Exp Cell Res 1988; 175:266-276). These results implied that the resistance against enzymatic degradation for the genipin-crosslinked microspheres is superior to the glutaraldehyde-crosslinked microspheres.

Crosslinking of gelatin microspheres with a crosslinking agent can limit their degradation rate and hydration potential, and therefore maintains their long-term release functions (Biomaterials 1996; 17:2009-2020; and Biomaterials 1994; 15:931-936). The increase in the resistance against degradation probably results from the cleavage sites of gelatin molecules being hidden or altered by the action of crosslinking, resulting in the inhibition of enzyme-substrate interaction. Moreover, crosslinking may hinder the penetration of enzymes into microspheres. As shown in FIG. 9, the heterocyclic crosslinking structure of the genipin-crosslinked microspheres may have a higher stereohindrance for the penetration of enzymes than the network crosslinking structure of the glutaraldehyde-crosslinked microspheres, due to the bulky heterocyclic-structure of genipin. The structure of stereohindrance may prevent enzymes from binding the substrates in gelatin molecules. Therefore, the degradation rate of the genipin-crosslinked microspheres was significantly slower than the glutaraldehyde-crosslinked microspheres.

The results obtained in the study suggested that crosslinking of gelatin microspheres with glutaraldehyde or genipin may produce distinct crosslinking structures. The differences in crosslinking structure may affect the dynamic swelling, water transport mechanism, and resistance against enzymatic degradation of the crosslinked microspheres. The drug-released characteristics of the genipin-crosslinked gelatin microspheres are currently under investigation.

Crosslinkers and Crosslinking

Previously, Chang in U.S. Pat. No. 5,929,038 discloses a method for treating hepatitis B viral infection with an iridoid compound of a general formula containing a six-member hydrocarbon ring sharing with one common bondage of a five-member hydrocarbon ring. Further, Moon et al. in U.S. Pat. No. 6,162,826 and No. 6,262,083 discloses genipin derivatives having anti hepatitis B virus activity and liver protection activity. All of which three aforementioned patents are incorporated herein by reference. The teachings of these patents do not disclose preparing a drug carrier that is chemically modified by genipin, genipin derivatives or its analog with acceptably minimal cytotoxicity.

Noishiki et al. in U.S. Pat. No. 4,806,595 discloses a tissue treatment method by a crosslinking agent, polyepoxy compounds. Collagens disclosed for use in that patent include an insoluble collagen, a soluble collagen, an atelocollagen prepared by removing telopeptides on the collagen molecule terminus using protease other than collagenase, a chemically modified collagen obtained by succinylation or esterification of above-described collagens, a collagen derivative such as gelatin, a polypeptide obtained by hydrolysis of collagen, and a natural collagen present in natural tissue (ureter, blood vessel, pericardium, heart valve, etc.) The Noishiki et al. patent is incorporated herein by reference. "Biological material" in the present invention is additionally used herein to refer to the above-mentioned collagens, collagen species, collagen in natural tissue, and collagen in a biological implant preform that are shapeable or fabricatable.

Voytik-Harbin et al. in U.S. Pat. No. 6,264,992 discloses submucosa as a growth substrate for cells. More particularly, the submucosa is enzymatically digested and gelled to form a shape retaining gel matrix suitable for inducing cell proliferation and growth both in vivo and in vitro. The Voytik-Harbin et al. patent is incorporated herein by reference. Biological material, additionally including submucosa, that is chemically modified or treated by genipin or other crosslinker of the present invention may serve as a shapeable raw material for making a biological substance adapted for inducing cell proliferation and ingrowth, but also resisting enzymatic degradation, both in vivo and in vitro. In a further aspect of the present invention, drug is loaded with submucosa biological material and crosslinked with a crosslinker, such as genipin.

Cook et al. in U.S. Pat. No. 6,206,931 discloses a graft prosthesis material including a purified, collagen-based matrix structure removed from a submucosa tissue source, wherein the submucosa tissue source is purified by disinfection and removal steps to deactivate and remove contaminants. The Cook et al. patent is incorporated herein by reference. Similarly, a collagen, elastin chitosan or gelatin-based matrix structure, also known as "biological material" in this invention, may serve as a biomaterial adapted for medical device use after chemical modification by genipin of the present invention.

Levene et al. in U.S. Pat. No. 6,103,255 discloses a porous polymer scaffold for tissue engineering, whereby the scaffold is characterized by a substantially continuous solid phase, having a highly interconnected bimodal distribution of open pore sizes. The Levene et al. patent is incorporated herein by reference. The present invention discloses biological scaffold material by acellular process and acidic/enzymatic treatment adapted for tissue engineering. Additional benefits of genipin tissue treatment for reduced antigenicity, reduced cytotoxicity and enhanced biodurability on a drug-containing biological substance are disclosed in the present invention. In one aspect, the porosity of a porous scaffold could be applied to the drug-loaded gelatin microspheres for controlled drug diffusion.

Biological Material-Drug-Genipin Compound

In one embodiment of the present invention, it is disclosed that a method for treating tissue of a patient comprising, in combination, loading a solidifiable drug-containing biological material onto a medical device or as a biological material without the additional device, solidify the drug-containing biological material, and chemically treating the drug-containing biological material with a crosslinking agent.

In another embodiment of the present invention, it is disclosed a biological substance for treating tissue of a patient with drug slow release, wherein the biological substance is made of drug-containing biological material that is solidifiable upon change of environmental condition(s) and is biocompatible after crosslinked with a crosslinker, such as genipin, epoxy compounds, dialdehyde starch, glutaraldehyde, or the like. The final drug-containing compound of the present invention could be in a generally spherical or non-spherical configuration.

In still another embodiment of the present invention, it is disclosed that a method for treating tissue of a patient comprising, in combination, mixing a drug with a solidifiable biological material, chemically treating the drug with the biological material with a crosslinking agent, and solidify the drug-containing biological material. In some aspect of the present invention, the method may further comprise loading the solidifiable drug-containing biological material onto a medical device prior to or after crosslinking step.

It is one continued aspect of the present invention that the method further comprises chemically linking the drug with the biological material, wherein the drug comprises at least a crosslinkable functional group with a specific crosslinker (for example, genipin), wherein the crosslinkable functional group may be, for example, an amino group.

Drug for Use in Biological Material-Drug-Genipin Compound

The drugs used in the current generation drug eluting cardiovascular stents include two major mechanisms: cytotoxic and cytostatic. Some aspects of the invention relating to the drugs used in collagen-drug-genipin compound from the category of cytotoxic mechanism comprise actinomycin D, paclitaxel, vincristin, methotrexate, and angiopeptin. Some aspects of the invention relating to the drugs used in collagen-drug-genipin compound from the category of cytostatic mechanism comprise batimastat, halofuginone, sirolimus, tacrolimus, everolimus, tranilast, dexamethasone, and mycophenolic acid (MPA). Some aspects of the present invention provide a bioactive agent in a bioactive agent-eluting device (i.e., one category of the drug-eluting device), wherein the bioactive agent is selected from a group consisting of actinomycin D, paclitaxel, vincristin, methotrexate, and angiopeptin, batimastat, halofuginone, sirolimus, tacrolimus, everolimus, tranilast, dexamethasone, and mycophenolic acid.

Everolimus with molecular weight of 958 (a chemical formula of $C_{53}H_{83}NO_{14}$) is poorly soluble in water and is a novel proliferation inhibitor. There is no clear upper therapeutic limit of everolimus. However, thrombocytopenia occurs at a rate of 17% at everolimus trough serum concentrations above 7.8 ng/ml in renal transplant recipients (Expert Opin Investig Drugs 2002; 11(12):1845-1857). In a patient, everolimus binds to cytosolic immunophyllin FKBP12 to inhibit growth factor-driven cell proliferation. Everolimus has shown promising results in animal studies, demonstrating a 50% reduction of neointimal proliferation compared with a control bare metal stent.

Straub et al. in U.S. Pat. No. 6,395,300 discloses a wide variety of drugs that are useful in the methods and compositions described herein, entire contents of which, including a variety of drugs, are incorporated herein by reference. Drugs contemplated for use in the compositions described in U.S. Pat. No. 6,395,300 and herein disclosed include the following categories and examples of drugs and alternative forms of these drugs such as alternative salt forms, free acid forms, free base forms, and hydrates:

analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate);

antiasthmatics (e.g., ketotifen and traxanox);

antibiotics (e.g., neomycin, streptomycin, chloramphenicol, cephalosporin, ampicillin, penicillin, tetracycline, and ciprofloxacin);

antidepressants (e.g., nefopam, oxypertine, doxepin, amoxapine, trazodone, amitriptyline, maprotiline, phenelzine, desipramine, nortriptyline, tranylcypromine, fluoxetine, doxepin, imipramine, imipramine pamoate, isocarboxazid, trimipramine, and protriptyline);

antidiabetics (e.g., biguamides and sulfonylurea derivatives);

antifungal agents (e.g., griseofulvin, ketoconazole, itraconizole, amphotericin B, nystatin, and candicidin);

antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine);

anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone);

antineoplastics (e.g., cyclophosphamide, actinomycin, bleomycin, daunorubicin, doxorubicin hydrochloride, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, piposulfan,);

antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene);

immunosuppressive agents (e.g., cyclosporine, azathioprine, mizoribine, and FK506 (tacrolimus));

antimigraine agents (e.g., ergotamine, propanolol, isometheptene mucate, and dichloralphenazone);

sedatives/hypnotics (e.g., barbiturates such as pentobarbital, pentobarbital, and secobarbital; and benzodiazapines such as flurazepam hydrochloride, triazolam, and midazolam);

antianginal agents (e.g., beta-adrenergic blockers; calcium channel blockers such as nifedipine, and diltiazem; and nitrates such as nitroglycerin, isosorbide dinitrate, pentaerythritol tetranitrate, and erythrityl tetranitrate);

antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine);

antimanic agents (e.g., lithium carbonate);

antiarrhythmics (e.g., bretylium tosylate, esmolol, verapamil, amiodarone, encamide, digoxin, digitoxin, mexiletine, disopyramide phosphate, procainamide, quinidine sulfate, quinidine gluconate, quinidine polygalacturonate, flecamide acetate, tocamide, and lidocaine);

antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium);

antigout agents (e.g., colchicine, and allopurinol);

anticoagulants (e.g., heparin, heparin sodium, and warfarin sodium);

thrombolytic agents (e.g., urokinase, streptokinase, and alteplase);

antifibrinolytic agents (e.g., aminocaproic acid);

hemorheologic agents (e.g., pentoxifylline);

antiplatelet agents (e.g., aspirin);

anticonvulsants (e.g., valproic acid, divalproex sodium, phenyloin, phenyloin sodium, clonazepam, primidone, phenobarbitol, carbamazepine, amobarbital sodium, methsuximide, metharbital, mephobarbital, mephenyloin, phensuximide, paramethadione, ethotoin, phenacemide, secobarbitol sodium, clorazepate dipotassium, and trimethadione);

antiparkinson agents (e.g., ethosuximide);

antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and);

agents useful for calcium regulation (e.g., calcitonin, and parathyroid hormone);

antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate);

antiviral agents (e.g., interferon alpha, beta or gamma, zidovudine, amantadine hydrochloride, ribavirin, and acyclovir);

antimicrobials (e.g., cephalosporins such as cefazolin sodium, cephradine, cefaclor, cephapirin sodium, ceftizoxime sodium, cefoperazone sodium, cefotetan disodium, cefuroxime azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin);

anti-infectives (e.g., GM-CSF);

bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate;

steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium);

hypoglycemic agents (e.g., human insulin, purified beef insulin, purified pork insulin, glyburide, chlorpropamide, glipizide, tolbutamide, and tolazamide);

hypolipidemic agents (e.g., clofibrate, dextrothyroxine sodium, probucol, pravastitin, atorvastatin, lovastatin, and niacin);

proteins (e.g., DNase, alginase, superoxide dismutase, and lipase);

nucleic acids (e.g., sense or anti-sense nucleic acids encoding any therapeutically useful protein, including any of the proteins described herein);

agents useful for erythropoiesis stimulation (e.g., erythropoietin);

antiulcer/antireflux agents (e.g., famotidine, cimetidine, and ranitidine hydrochloride);

antinauseants/antiemetics (e.g., meclizine hydrochloride, nabilone, prochlorperazine, dimenhydrinate, promethazine hydrochloride, thiethylperazine, and scopolamine);

as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, metformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, monteleukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. These drugs are generally considered to be water soluble.

Preferred drugs useful in the present invention may include albuterol, adapalene, doxazosin mesylate, mometasone furoate, ursodiol, amphotericin, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, omeprazole, rubitecan, amlodipine besylate/benazepril hydrochloride, etodolac, paroxetine hydrochloride, paclitaxel, atovaquone, felodipine, podofilox, paricalcitol, betamethasone dipropionate, fentanyl, pramipexole dihydrochloride, Vitamin $D_3$ and related analogues, finasteride, quetiapine fumarate, alprostadil, candesartan, cilexetil, fluconazole, ritonavir, busulfan, carbamazepine, flumazenil, risperidone, carbemazepine, carbidopa, levodopa, ganciclovir, saquinavir, amprenavir, carboplatin, glyburide, sertraline hydrochloride, rofecoxib carvedilol, clobustasol, diflucortolone, halobetasolproprionate, sildenafil citrate, celecoxib, chlorthalidone, imiquimod, simvastatin, citalopram, ciprofloxacin, irinotecan hydrochloride, sparfloxacin, efavirenz, cisapride monohydrate, lansoprazole, tamsulosin hydrochloride, mofafinil, clarithromycin, letrozole, terbinafine hydrochloride, rosiglitazone maleate, diclofenac sodium, lomefloxacin hydrochloride, tirofiban hydrochloride, telmisartan, diazepam, loratadine, toremifene citrate, thalidomide, dinoprostone, mefloquine hydrochloride, trandolapril, docetaxel, mitoxantrone hydrochloride, tretinoin, etodolac, triamcinolone acetate, estradiol, ursodiol, nelfinavir mesylate, indinavir, beclomethasone dipropionate, oxaprozin, flutamide, famotidine, nifedipine, prednisone, cefuroxime, lorazepam, digoxin, lovastatin, griseofulvin, naproxen, ibuprofen, isotretinoin, tamoxifen citrate, nimodipine, amiodarone, and alprazolam.

Specific non-limiting examples of some drugs that fall under the above categories include paclitaxel, docetaxel and derivatives, epothilones, nitric oxide release agents, heparin, aspirin, coumadin, PPACK, hirudin, polypeptide from angiostatin and endostatin, methotrexate, 5-fluorouracil, estradiol, P-selectin Glycoprotein ligand-1 chimera, abciximab, exochelin, eleutherobin and sarcodictyin, fludarabine, sirolimus, tranilast, VEGF, transforming growth factor (TGF)-beta, Insulin-like growth factor (IGF), platelet derived growth factor (PDGF), fibroblast growth factor (FGF), RGD peptide, beta or gamma ray emitter (radioactive) agents, and dexamethasone, tacrolimus, actinomycin-D, batimastat etc.

Sirolimus is naturally occurring macrolide antibiotic produced by the fungus *Streptomyces* found in Easter Island. It was discovered by Wyeth-Ayerst in 1974 while screening fermentation products. Sirolimus with molecular weight of 916 (a chemical formula of $C_{51}H_{79}NO_{13}$) is non-water soluble and is a potential inhibitor of cytokine and growth factor mediated cell proliferation. FDA approved its use as oral immunosuppressive agents with a formulation of 2 to 5 mg/dose. The suggested drug-eluting efficacy is about 140 micrograms/cm$^2$, 95% drug release at 90 days and 30% drug-to-polymer ratio.

In some aspect of the present invention, the drug may broadly comprise, but not limited to, synthetic chemicals, biotechnology-derived molecules, herbs, health food, extracts, and/or alternate medicines; for example, including allicin and its corresponding garlic extract, ginsenosides and the corresponding ginseng extract, flavone/terpene lactone and the corresponding *ginkgo biloba* extract, glycyrrhetinic acid and the corresponding licorice extract, and polyphenol/proanthocyamides and the corresponding grape seed extract.

While the preventive and treatment properties of the foregoing therapeutic substances, agents, drugs, or bioactive agents are well known to those having ordinary skill in the art, the substances or agents are provided by way of example and are not meant to be limiting. Other therapeutic substances are equally applicable for use with the disclosed methods, devices, and compositions.

In the present invention, the terms "crosslinking", "fixation", "chemical modification", and "chemical treatment" for tissue, collagen, or biological material are used interchangeably.

FIG. 11 shows chemical structures of glutaraldehyde and genipin that are used in the chemical treatment examples of the current invention. Other crosslink agent may equally be applicable for collagen-drug-heparin compound disclosed herein.

Other than genipin and glutaraldehyde, the crosslinking agent that may be used in chemical treatment of the present invention may include formaldehyde, dialdehyde starch, glyceraldehydes, cyanamide, diimides, diisocyanates, dimethyl adipimidate, epoxy compound and the like.

Glutaraldehyde Crosslinking

Glutaraldehyde has been used extensively as a crosslinking agent for fixing biologic tissues. By means of its aldehyde functional groups, glutaraldehyde reacts primarily with the E-amino groups of lysyl or hydroxylysyl residues within biologic tissues. The mechanism of fixation of biologic tissues or biologic matrix with glutaraldehyde can be found elsewhere (Nimni M E et al. in Nimni M E, editor. COLLAGEN. Vol. 111. Boca Raton (Fla.); CRC Press 1998. pp. 1-38). Polymerization of glutaraldehyde molecules in aqueous solution with observable reductions in free aldehyde have been reported previously (Nimni M E et al. in Nimni M E, editor. COLLAGEN. Vol. 111. Boca Raton (Fla.); CRC Press 1998. pp. 1-38). In polymerization the aldehyde functional groups of 2 glutaraldehyde molecules may undergo an aldol condensation. With glutaraldehyde polymerization, subsequent to fixation, a network crosslinking structure could conceivably be created intramolecularly and intermolecularly within collagen fibers.

It is conceivable that a substance (for example, a drug) having an amine or amino functional group may react with glutaraldehyde as illustrated above. By combining collagen, glutaraldehyde and a drug having an amine or amino group, the crosslinked compound may link collagen to the drug via glutaraldehyde as a crosslinker.

Crosslinking of a Polymer Having an Amine Group

Several biocompatible plastic polymers or synthetic polymers have one or more amine group in their chemical structures. The amine group may become reactive toward a crosslinker, such as glutaraldehyde or genipin or epoxy compounds. Therefore, it is conceivable that by combining a polymer having an amine group, glutaraldehyde and a drug having at least an amine or amino group, the crosslinked compound may have the polymer linked to the drug via glutaraldehyde as a crosslinker.

Genipin Crosslinking

It was found by Sung H W (Biomaterials 1999; 20:1759-72) that genipin can react with the free amino groups of lysine, hydroxylysine, or arginine residues within biologic tissues. Touyama et al. (Chem Pharm Bull 1994; 42:668-673) studied the structures of the intermediates, leading to a blue pigment produced from genipin and methylamine, the simplest primary amine. The mechanism was suggested that the genipin-methylamine monomer is formed through a nucleophilic attack by methylamine on the olefinic carbon at C-3 of genipin, followed by opening of the dihydropyran ring and attack by the secondary amino group on the resulting aldehyde group. The blue-pigment was thought formed through oxygen radical-induced polymerization and dehydrogenation of several intermediary pigments.

As disclosed by Sung et al. (J Thorac Cardiovasc Surg 2001; 122:1208-1218) and reported by Fujikawa et al. (Agric Biol Chem 1988; 52:869-870), the simplest component in the blue pigment was a 1:1 adduct. It was suggested that genipin reacts spontaneously with an amino acid to form a nitrogen iridoid, which undergoes dehydration to form an aromatic monomer. Dimerization occurs at the second stage, perhaps by means of radical reaction. The results suggest that genipin may form intramolecular and intermolecular crosslinks with cyclic structure within collagen fibers in biologic tissue or solidifiable collagen-containing biological material.

It is disclosed herein that genipin is capable of reacting with a drug having an amine or amino group. By combining collagen (or a biological material or matrix), genipin and the drug having an amine or amino group, the crosslinked compound may have collagen linked to the drug via genipin as a crosslinker.

As disclosed and outlined in U.S. Pat. No. 6,545,042 issued on Apr. 8, 2003 entitled "Acellular biological material chemically treated with genipin" by two of the present inventors, the degrees in inflammatory reaction in the animal studies for the genipin-fixed cellular and acellular tissue were significantly less than their glutaraldehyde-fixed counterparts. Additionally, it was noted that the inflammatory reactions for the glutaraldehyde-fixed cellular and acellular tissue lasted significantly longer than their genipin-fixed counterparts. These findings indicate that the biocompatibility of the genipin-fixed cellular and acellular tissue is superior to the glutaraldehyde-fixed cellular and acellular tissue. It is hypothesized that the lower inflammatory reactions observed for the genipin-fixed cellular and acellular tissue may be due to the lower cytotoxicity of their remaining residues, as compared to the glutaraldehyde-fixed counterparts. In a previous study, it was found that genipin is significantly less cytotoxic than glutaraldehyde (J Biomater Sci Polymer Edn 1999; 10:63-78). The cytotoxicity observed for the glutaraldehyde-fixed cellular and acellular tissue seems to result from a slow leaching out of unreacted glutaraldehyde as well as the reversibility of glutaraldehyde-crosslinking. It was observed that when concentrations above 0.05% glutaraldehyde were used to crosslink materials, a persistent foreign-body reaction occurred (J Biomater Sci Polymer Edn 1999; 10:63-78).

EXAMPLE #4

Dissolve chitosan powder in acetic acid at about pH 4. Chitosan (MW: about 70,000) was purchased from Fluka Chemical Co. of Switzerland. The deacetylation degree of the chitosan used was approximately 85%. Add in drug(s) of interest into the chitosan solution. While loading the drug-containing chitosan onto a stent, adjust the environment to pH 7 with NaOH to solidify the chitosan onto the stent. The process can be accomplished via a continuous assembly line step by providing gradually increasing pH zones as the device passes by. It is further treated with a crosslinking agent, for example genipin to enhance the biodurability and biocompatibility. Note that the chemical formula for chitosan can be found in Mi F L, Tan Y C, Liang H F, and Sung H W, *In vivo biocompatibility and degradability of a novel injectable-chitosan based implant* (Biomaterials 2002; 23:181-191).

EXAMPLE #5

Dissolve collagen in a low temperature of about 4° C. Add in drug(s) of interest into the collagen solution. While loading the drug-containing collagen onto a stent, adjust the environment temperature to about 37° C. to solidify the collagen onto the stent. The process can be accomplished via a continuous assembly line step by providing gradually increasing temperature zones as the device passes by. The loading step can be repeated a few times to increase the thickness or total quantity of the drug-containing collagen. The loading step can be started with a high-does drug-containing collagen and then loaded with a lower dose drug-containing collagen or vice versa. It is further treated with a crosslinking agent, for example genipin to enhance the biodurability and biocompatibility. The fixation details could be found elsewhere by Sung et al. (Sung H W, Chang Y, Liang I L, Chang W H and Chen Y C, *Fixation of biological tissues with a naturally occurring crosslinking agent: fixation rate and effects pf pH, temperature, and initial fixative concentration*. J Biomed Mater Res 2000; 52:77-87).

EXAMPLE #6

Add drug and stent in a NOCC solution at room temperature. The NOCC (named after "Nitrogen Oxygen Carboxylmethyl chitosan") is a chitosan derived compound solution that is pH sensitive and can be used in drug delivery. This NOCC is water soluble at pH 7. Crosslink the NOCC and drug onto the stent by a crosslinking agent, for example genipin. After crosslinking, the drug containing NOCC can be made solid by low pH at about 4. The finished stent slowly releases drug when in the body at a pH around neutral.

EXAMPLE #7

Taxol (paclitaxel) is practically water insoluble as some other drugs of interest in this invention. Therefore, first mechanically disperse paclitaxel in a collagen solution at about 4° C. Load the drug containing collagen onto a stent and subsequently raise the temperature to about 37° C. to solidify collagen fibers on the stent. The loading step may repeat a plurality of times. Subsequently, crosslink the coated stent with aqueous genipin.

In a broader scope of the present invention, the "drug" further comprises bioactive agents or materials which may be used in the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, naked DNA, cDNA, RNA, DNA, cDNA, or RNA in a non-infectious vector or in a viral vector which may have attached peptide targeting sequences; anti-sense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application, including retrovirus, adenovirus, adeno-associated virus, herpes simplex virus, and the like.

For example, biologically active solutes include anti-thrombogenic agents such as heparin, heparin derivatives, urokinase, PPACK (dextrophenylalanine proline arginine chloromethylketone), rapamycin, probucol, and verapamil; angiogenic and anti-angiogenic agents; anti-proliferative agents such as enoxaparin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; anti-neoplastic/antiproliferative/anti-mitotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Arg chloromethyl keton, and RGD peptide-containing compound, heparin, antithrombin compounds, platelet receptor antagonists, anti-thrombin antibodies, antiplatelet receptor antibodies, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directly against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms, and combinations thereof. These and other compounds are applicable to the device and methods of the invention.

U.S. Pat. No. 6,423,682, issued on Jul. 23, 2002 and U.S. Pat. No. 6,485,920, issued on Nov. 26, 2002, the entire contents of both of which are incorporated herein by reference, disclose the compositions of novel human growth factor antagonist proteins and active variants thereof, isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies function of mitochondria and toxic substances synthesized as a metabolic byproduct within mitochondria of cells. Some aspects of the present invention provide a device comprising solidifiable bioactive agent-containing biological material loaded onto at least a portion of the surface of the device, followed by being crosslinked with a crosslinking agent, wherein the bioactive agent comprises at least one of the above-cited genes.

U.S. Pat. No. 6,476,211, issued on Nov. 5, 2002, the entire contents of which are incorporated herein by reference, discloses human CD39-like protein polynucleotides isolated from cDNA libraries of human fetal liver-spleen and macrophage as well as polypeptides encoded by these polynucleotides and mutants or variants thereof. CD39 (cluster of differentiation 39) is a cell-surface molecule recognized by a "cluster" of monoclonal antibodies that can be used to identify the lineage or stage of differentiation of lymphocytes and thus to distinguish one class of lymphocytes from another. Some aspects of the present invention provide a device comprising solidifiable bioactive agent-containing biological material loaded onto at least a portion of the surface of the device, followed by being crosslinked with a crosslinking agent, wherein the bioactive agent comprises the above-cited human CD39-like protein polynucleotides or the like.

U.S. Pat. No. 5,780,052, issued Jul. 14, 1998, the entire contents of which are incorporated herein by reference, discloses a method of salvaging a target cell from cell death, comprising contacting a target cell, having a disrupted cell membrane with a specific affinity reagent-liposome conjugate in, an amount effective and for a time sufficient to allow the conjugate to prevent cell death due to membrane disruption. The patent discloses methods of delivering a selected agent into a damaged target cell for diagnosis and therapy, wherein the conjugate comprises a biological agent selected from the group consisting of fibroblastic growth factor-β, angiogenic factors, high energy substrates for the myocardium, antioxidants, cytokines and contrast agents. Some aspects of the present invention provide a device comprising solidifiable bioactive agent-containing biological material loaded onto at least a portion of the surface of the device, followed by being crosslinked with a crosslinking agent, wherein the bioactive agent comprises the above-cited fibroblastic growth factor-β, angiogenic factors, high energy substrates for the myocardium, antioxidants, cytokines and the like.

U.S. Pat. No. 6,475,784, issued on Nov. 5, 2002, the entire contents of which are incorporated herein by reference, discloses a method for polypeptides having anti-angiogenic activity and nucleic acids that encode these polypeptides. The anti-angiogenic polypeptides include at least kringles 1-3 of plasminogen. The patent '784 also provides methods of using the polypeptides and nucleic acids for inhibiting angiogenesis and other conditions characterized by undesirable endothelial cell proliferation. Angiostatin, which is an angiogenesis inhibitor, is a naturally occurring internal cleavage product of plasminogen, wherein human plasminogen has five characteristic protein domains called "kringle structures". Some aspects of the present invention provide a device comprising solidifiable bioactive agent-containing biological material loaded onto at least a portion of the surface of the device, followed by being crosslinked with a crosslinking agent, wherein the bioactive agent comprises the above-cited anti-angiogenic polypeptides, angiostatin, angiogenesis inhibitor, and the like.

U.S. Pat. No. 6,436,703, issued on Aug. 20, 2002, the entire contents of which are incorporated herein by reference, discloses a method and compositions comprising novel isolated polypeptides, novel isolated polynucleotides encoding such polypeptides, including recombinant DNA molecules, cloned genes or degenerate variants thereof, especially naturally occurring variants such as allelic variants, antisense polynucleotide molecules, and antibodies that specifically recognize one or more epitopes present on such polypeptides, as well as hybridomas producing such antibodies. The compositions in '703 additionally include vectors, including expression vectors, containing the polynucleotides of the invention, cells genetically engineered to contain such polynucleotides and cells genetically engineered to express such polynucleotides. Some aspects of the present invention provide a device comprising solidifiable bioactive agent-containing biological material loaded onto at least a portion of the surface of the device, followed by being crosslinked with a crosslinking agent, wherein the bioactive agent comprises the above-cited antisense polynucleotide molecules and the like.

U.S. Pat. No. 6,451,764, issued on Sep. 17, 2002, the entire contents of which are incorporated herein by reference, discloses a method of treating vascular tissue and promoting angiogenesis in a mammal comprising administering to the mammal an effective amount of the composition comprising VRP (vascular endothelial growth factor-related protein). The invention '764 further provides a method for treating trauma affecting the vascular endothelium comprising administering to a mammal suffering from the trauma an effective amount of the composition containing the VRP, or a method for treating a dysfunctional state characterized by lack of activation or lack of inhibition of a receptor for VRP in a mammal. Some aspects of the present invention provide a device comprising solidifiable bioactive agent-containing biological material loaded onto at least a portion of the surface of the device, followed by being crosslinked with a crosslinking agent, wherein the bioactive agent comprises the above-cited inhibitors or receptors for vascular endothelial growth factor-related protein and the like.

Pharmaceutical Formulation

The invention provides pharmaceutical compositions that can be administered to a patient to achieve therapeutic effects with a microsphere-type drug carrier chemically treated with a crosslinker. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable ingredients comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers that are properly crosslinked and well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient and for drug slow-release.

Pharmaceutical preparations for oral use can be obtained through combination of active compounds with a crosslinkable biological material of the present invention and solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers. One aspect of the present invention is to provide a pharmaceutical preparation with push-fit capsules made of gelatin that is properly crosslinked.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes, followed by encapsulating with gelatin that is properly crosslinked. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1-50 mM histidine, 0.1%-2% sucrose, and 2-7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, including a step of encapsulating with gelatin that is properly crosslinked, they can be placed in an appropriate container and labeled for treatment of an indicated condition. Such labeling would include amount, frequency, and method of administration.

From the foregoing description, it should now be appreciated that a novel and unobvious process for making a biological substance comprising an illustrative gelatin-drug-genipin compound for drug slow release has been disclosed for therapeutic treatment applications. The process comprises, in combination, mixing a drug with a solidifiable biological material, chemically treating the biological material and/or the drug with a crosslinking agent, and solidify the drug-containing biological material. The resulting biological substance is generally characterized with reduced antigenicity, reduced immunogenicity, and reduced enzymatic degradation. While the invention has been described with reference to a specific embodiment, the description is illustrative of the invention and is not to be construed as limiting the invention. Various modifications and applications may occur to those who are skilled in the art, without departing from the true spirit and scope of the invention.

REFERENCES-LITERATURE

1. Ugwoke M I, and Kinget R. *Influence of processing variables on the properties of gelatin microspheres prepared by emulsification solvent extraction technique.* J Microencapsulation 1998; 15:273-281.
2. Li J K, Wang N, and Wu X S. *Gelatin nanoencapsulation of protein/peptide drugs using an emulsifier-free emulsion method.* J Microencapsulation 1998; 15:163-172.
3. Tabata Y, Hijikata S, Muniruzzaman M, and Ikada Y. *Neovascularization effect of biodegradable gelation microspheres incorporating basic fibroblast growth factor.* J Biomater Sci Polymer Edn 1999; 10:79-94.
4. Rowe J S, and Carless J E. *Comparison of the in vitro dissolution behavior of various indomethacin formulations with their in vivo bioavailability.* J Pharm Pharmacol 1981; 33:561-564.
5. Chiao C S L, and Price J C. *Modification of gelatin beadlets for zero-order sustained release.* Pharm Res 1989; 6:517-520.
6. Esposito E, Cortesi R, and Nastruzzi C. *Gelatin microspheres: Influence of preparation parameters and thermal treatment on chemico-physical and biopharmaceutical properties.* Biomaterials 1996; 17:2009-2020.
7. Ratcliffe J H, Hunneyball I M, Smith A, Wilson C G, and Pavis S S. *Preparation and evaluation of biodegradable polymeric system for the intra-particular delivery of drug.* J Pharm Pharmacol 1984; 36:431-436.
8. Leo E, Vandelli M A, Cameroni R, and Formi F. *Doxorubicin-loaded gelatin nanoparticles stabilized by glutaraldehyde: Involvement of the drug in the crosslinking process.* Int J Pharm 1997; 155:75-82.

9. Yan C, Li X, Chen X, Wang D, Zhong D, Tan T, and Kitano H. *Anticancer gelatin microspheres with multiple function*. Biomaterials 1991; 12:640-644.
10. Rao K P. *Recent developments of collagen-based materials for medical applications and drug delivery system*. J Biomater Sci Polymer Edn 1995; 7:623-645.
11. Silvio L D, Gurav N, Kayser M V, Braden M, and Downes S. *Biodegradable microspheres: A new delivery system for growth hormone*. Biomaterials 1994; 15:931-936.
12. Hazel B, Roy 0, and Roy G. *Formaldehyde as a pre-treatment for dermal collagen heterografts*. Biochimica et Biophysica Acta 1980; 632:589-597.
13. Gendler E, Gendler S, and Nimni M E, *Toxic reactions evoked by glutaraldehyde-fixed pericardium and cardiac valve tissue bioprosthesis*. J Biomed Mater Res 1984; 18:727-736.
14. Akao T, Kobashi K, and Aburada M. *Enzymatic studies on the animal and intestinal bacterial metabolism of geniposide*. Biol Pharm Bull 1994; 17:1573-1576.
15. Touyama R, Takeda Y, Inoue K, Kawamura I, Yatsuzuka M, Ikumoto T, Shingu T, Yokoi T, and Inouye H. *Studies on the blue pigments produced from genipin and methylamine. I. Structures of the brownish-red pigments, intermediates leading to the blue pigments*. Chem Pharm Bull 1994; 42:668-673.
16. Touyama R, Inoue K, Takeda Y, Yatsuzuka M, Ikumoto T, Moritome N, Shingu T, Yokoi T, and Inouye H. *Studies on the blue pigments produced from genipin and methylamine. II. On the formation mechanisms of brownish-red intermediates leading to the blue pigment formation*. Chem Pharm Bull 1994; 42:1571-1578.
17. Sung H W, Huang R N, Huang L L H, Tsai C C, and Chiu C T. *Feasibility study of a natural crosslinking reagent for biological tissue fixation*. J Biomed Mater Res 1998; 42:560-67.
18. Sung H W, Huang D M, Chang W H, Huang R N, and Hsu J C. *Evaluation of gelatin hydrogel crosslinked with various crosslinking agents as bioadhesives: In vitro study*. J Biomed Mater Res 1999; 46:520-530.
19. Sung H W, Huang D M, Chang W H, Huang L L H, Tsai C C, and Liang I L. *Gelatin-derived bioadhesives for closing skin wounds: An in vivo study*. J Biomater Sci Polymer Edn 1999; 10:751-771.
20. Tanaka N, Takino S, and Utsumi I. *A new oral gelatinized sustained-release dosage form*. J Pharm Sci 1963; 52:664-667.
21. Stryer L. Biochemistry, 3rd ed. New York: Freeman, 1988, p. 50-55.
22. Robert C C R, Buri P A, and Peppas N A. *Influence of the drug solubility and dissolution medium on the release from poly(2-hydroxyethyl methacrylate) microspheres*. J Controlled Release 1987; 5:151-157.
23. Vandelli M A, Fomi F, Coppi G, and Cameroni R. *The effect of the cross-linking time period upon the drug release and the dynamic swelling of gelatin microspheres*. Pharmazie 1991; 46:866-869.
24. Courtman D W, Errett B F, and Wilson G J. *The role of crosslinking in modification of the immune response elicited against xenogenic vascular acellular matrices*. J Biomed Mater Res 2001; 55:576-86.
25. Madan P L, Luzzi L A, and Price C J. *Microencapsulation of a waxy solid: Wall thickness and surface appearance studies*. J Pharm Sci 1974; 63:409-411.
26. Raymond G, Degennaro M, and Mikeal R. *Preparation of gelatin: phenyloin sodium microspheres: An in vitro and in vivo evaluation*. Drug Dev Ind Pharm 1990; 16:1025-1051.
27. Narayani R, and Rao K P. *Controlled release of anticancer drug methotrexate from biodegradable gelatin microspheres*. J Microencapsulation 1994; 11:69-77.
28. Luzzi L A, and Gerraughty R J. *Effect of additives and formulation techniques on controlled release of drug from microcapsules*. J Pharm Sci 1967; 9:1174-1177.
29. Speer D P, Chvapil M, Eskelson C D, and Ulreich J. *Biological effects of residual glutaraldehyde in glutaraldehyde-tanned collagen biomaterials*. J Biomed Mater Res 1980; 14:753-764.
30. Nimni M E, Cheung D, Strates B, Kodama M, and Sheikh K *Bioprosthesis derived from crosslinked and chemically modified collagenous tissues*. In: Nimni M E, editor. Collagen, Vol. III. Boca Raton, Fla.: CRC Press, 1988: pp. 1-38.
31. Bowes J H, and Cater C W. *The reaction of glutaraldehyde with proteins and other biological materials*. J R Microsc Soc 1966; 85:193-200.
32. Jayakrishnan A, and Jameela S R. *Glutaraldehyde as a fixative in bioprostheses and drug delivery matrices*. Biomaterials 1996; 17:471-84.
33. Lee P I. *Kinetics of drug release from hydrogel matrices*. J Control Rel 1985; 2:277-288.
34. Sung H W, Huang R N, Huang L L H, and Tsai C C. *In vitro evaluation of cytotoxicity of a naturally occurring crosslinking reagent for biological tissue fixation*. J Biomater Sci Polymer Edn 1999; 10:63-78.
35. Nimni M E, and Harkness R D. *Molecular structure and function of collagen*. In: Nimni M E, editor. Collagen, Vol. I. Boca Raton, Fla.: CRC Press; 1988. p 1-77.
36. Scott R, Baraza R, Gorham S D, McGregor I, and French D A. *Assessment of collagen film for use in urinary tract surgery*. Brit J Urol 1986; 58:203-207.
37. Gorham S D, Hyland T P, French D A, and Willins M J. *Cellular invasion and breakdown of three different collagen films in the lumbar muscle of the rat*. Biomaterials 1990; 11:113-118.
38. Silver I A, Murills R J, and Etherington D J. *Microelectrode studies on the acid microenvironment beneath macrophages and osteoclasts*. Exp Cell Res 1988; 175:266-276.
39. Sung H W, Chang Y, Chiu C T, Chen C N, and Liang H C. *Mechanical properties of a porcine aortic valve fixed with a naturally occurring crosslinking agent*. Biomaterials 1999; 20: 1759-72.
40. Tsai C C, Huang R N, Sung H W, and Liang H C. *In vitro evaluation of the genotoxicity of a naturally occurring crosslinking agent (genipin) for biological tissue fixation*. J Biomed Mater Res 2000; 52:58-65.
41. Sung H W, Hsu C S, Lee Y S, and Lin D S. *Crosslinking characteristics of an epoxy-fixed porcine tendon: Effects of pH, temperature, and fixative concentration*. J Biomed Mater Res 1996; 31:511-8.
42. Mi F L, Sung H W, and Shyu S S. "*Synthesis and characterization of TPP/genipin crosslinked chitosan gel beads*. J Polymer Science, Part A: Polymer Chemistry (submitted)
43. Sung H W, Chang W H, Ma C Y, and Lee M H. *Crosslinking of biological tissues using genipin and/or carbodiimide*. J Bomed Mater Res (submitted)

44. Chang Y, Tsai C C, Liang H C, and Sung H W. *In vivo evaluation of cellular and acellular bovine pericardia fixed with a naturally occurring crosslinking agent (genipin).* Biomaterials (in press)
45. Mi F L, Sung H W, Lee S T, and Shyu S S. *Drug release from chitosan alginate complex beads reinforced by a naturally occurring crosslinking agent.* Carbohydrate Polymers 2002; 48:61-72
46. Mi F L, Tan Y C, Liang H F, and Sung H W. *In vivo biocompatibility and degradability of a novel injectable-chitosan based implant.* Biomaterials 2002; 23:181-191
47. Mi F L, Tan Y C, Liang H C, Huang R N, and Sung H W. *In vitro evaluation of a chitosan membrane crosslinked with genipin.* J Biomaterials Sci-Polymer edition 2001; 12:835-850
48. Mi F L, Sung H W, Liu S M, and Shyu S S. *Release of indomethacin from a novel chitosan microsphere prepared by a naturally occurring crosslinker: examination of crosslinking and polycation-anion drug interaction.* J Appl Polymer Sci 2001; 81:1700-1711
49. Chang Y, Tsai C C, Liang H C and Sung H W. *Reconstruction of the right ventricular outflow tract with a bovine jugular vein graft fixed with a naturally occurring crosslinking agent (genipin) in a canine model.* J Thorac Cardiovasc Surg 2001; 122:1208-1218
50. Sung H W, Chang Y, Liang I L, Chang W H and Chen Y C. *Fixation of biological tissues with a naturally occurring crosslinking agent: fixation rate and effects pf pH, temperature, and initial fixative concentration.* J Biomed Mater Res 2000; 52:77-87
51. Liang H C, Chang W H, Lin K J and Sung H W. *Genipin-crosslinked gelatin microspheres as a drug carrier for intramuscular administration: in vitro and in vivo studies.* J Biomed Mater Res 2003; 65A:271-282.

What is claimed is:

1. A method for administering a pharmaceutical microsphere into a body of a patient comprising:
    providing the pharmaceutical microsphere that comprises heparin and a gelatin carrier, said gelatin carrier encapsulating said heparin, wherein the gelatin carrier is crosslinked with genipin and wherein a degree of crosslinking for the crosslinked gelatin with genipin is about 60%; and
    delivering said pharmaceutical microsphere into the body.
2. The method of claim 1, wherein said delivering is carried out orally for the patient.
3. The method of claim 1, wherein said delivering is carried out via intramuscular administration for the patient.
4. The method of claim 1, wherein said microsphere has an average diameter between 20 and 100 µm.
5. The method of claim 1, wherein said microsphere is prepared by an emulsification-solvent-extraction method.
6. The method of claim 1, wherein said microsphere is manufactured by a spray drying process.

* * * * *